(12) United States Patent
Mlodzinski et al.

(10) Patent No.: US 7,931,859 B2
(45) Date of Patent: Apr. 26, 2011

(54) ULTRAVIOLET SANITIZATION IN PHARMACY ENVIRONMENTS

(75) Inventors: Lance R. Mlodzinski, Winnipeg (CA); Walter W. Eliuk, Winnipeg (CA); Alex H. Reinhardt, St. Andrews (CA); Ronald H. Rob, Dugald (CA); Robert Keith Davidson, Winnipeg (CA)

(73) Assignee: Intelligent Hospital Systems Ltd., Winnipeg, Manitoba (CA)

( * ) Notice: Subject to any disclaimer, the term of this patent is extended or adjusted under 35 U.S.C. 154(b) by 465 days.

(21) Appl. No.: 12/035,850

(22) Filed: Feb. 22, 2008

(65) Prior Publication Data

US 2008/0199353 A1    Aug. 21, 2008

Related U.S. Application Data

(63) Continuation-in-part of application No. 11/937,846, filed on Nov. 9, 2007, and a continuation-in-part of application No. 11/389,995, filed on Mar. 27, 2006, now Pat. No. 7,783,383, and a continuation-in-part of application No. 11/316,795, filed on Dec. 22, 2005, now Pat. No. 7,610,115.

(60) Provisional application No. 60/988,660, filed on Nov. 16, 2007, provisional application No. 60/971,815, filed on Sep. 12, 2007, provisional application No. 60/891,433, filed on Feb. 23, 2007.

(51) Int. Cl.
| | |
|---|---|
| *A61L 2/00* | (2006.01) |
| *B01J 19/08* | (2006.01) |
| *G01N 23/00* | (2006.01) |
| *A61N 5/00* | (2006.01) |
| *A61B 18/18* | (2006.01) |
| *A61B 19/00* | (2006.01) |
| *A61M 1/00* | (2006.01) |
| *B65G 59/00* | (2006.01) |

(52) U.S. Cl. .......... 422/24; 422/1; 422/22; 422/121; 422/186; 422/186.3; 422/305; 250/455.11; 250/492.1; 250/435; 606/15; 606/7; 221/123; 221/130; 604/29; 604/411; 604/905

(58) Field of Classification Search .......... 422/1, 22, 422/24, 121, 186, 186.3, 305; 250/455.11, 250/492.1, 435; 606/15, 7; 221/123, 130; 604/29, 411, 905
See application file for complete search history.

(56) References Cited

U.S. PATENT DOCUMENTS 2,275,788 A * 3/1942 Meeker et al. .......... 250/455.11
(Continued)

FOREIGN PATENT DOCUMENTS

CA    1317262    5/1993
(Continued)

OTHER PUBLICATIONS

Office Action in Re Exam Control No. 95/000,335; mailed Oct. 1, 2009 27 pages.
(Continued)

*Primary Examiner* — Jill Warden
*Assistant Examiner* — Monzer R Chorbaji

(57) ABSTRACT

Systems and methods to reduce bioburden on at least a portion of a fluid transfer port include supplying a dose of radiation to the portion in optical communication with at least one source of radiation. In an illustrative example, a medical container, such as a vial or IV bag, receives a dose of ultraviolet (UV) energy substantially at a predetermined region of a fluid transfer site. In some examples, such a sanitization process may precede a fluid transfer operation in which a fluid is transferred into or out of the medical container by passing through the sanitized region. Such fluid transfers may be used in automated or semi-automated pharmaceutical processes, such as drug reconstitution. Various embodiments may further include one or more seal assemblies, each seal assembly having an aperture through which the radiation dose is supplied from the source to a controlled region on the fluid transfer port.

56 Claims, 14 Drawing Sheets

U.S. PATENT DOCUMENTS

| | | | |
|---|---|---|---|
| 2,988,984 A | 6/1961 | Eckert et al. | |
| 3,002,387 A | 10/1961 | Micheletti | |
| 3,556,342 A | 1/1971 | Guarr | |
| 3,878,967 A | 4/1975 | Joslin et al. | |
| 3,880,211 A | 4/1975 | Gess | |
| 3,965,945 A | 6/1976 | Ross | |
| 4,058,121 A | 11/1977 | Choksi et al. | |
| 4,372,464 A | 2/1983 | Otten | |
| 4,464,336 A | 8/1984 | Hiramoto | |
| 4,634,424 A | 1/1987 | O'Boyle | |
| 4,648,430 A | 3/1987 | Di Gianfilippo et al. | |
| 4,669,599 A | 6/1987 | Dijkmeijer et al. | |
| 4,699,186 A | 10/1987 | Palin et al. | |
| 4,706,207 A | 11/1987 | Hennessy et al. | |
| 4,730,435 A | 3/1988 | Riddle et al. | |
| 4,811,764 A | 3/1989 | McLaughlin | |
| 4,829,524 A | 5/1989 | Yoshida | |
| 4,835,372 A | 5/1989 | Gombrich et al. | |
| 4,835,707 A | 5/1989 | Amano et al. | |
| 4,842,028 A * | 6/1989 | Kaufman et al. | 141/114 |
| 4,847,764 A | 7/1989 | Halvorson | |
| 4,861,335 A | 8/1989 | Reynolds | |
| 4,871,559 A | 10/1989 | Dunn et al. | |
| 4,878,705 A | 11/1989 | Arnquist | |
| 4,910,942 A | 3/1990 | Dunn et al. | |
| 4,918,604 A | 4/1990 | Baum | |
| 4,993,598 A | 2/1991 | Groninger | |
| 5,004,962 A | 4/1991 | Fonss et al. | |
| 5,020,958 A | 6/1991 | Tuttobene | |
| 5,034,235 A | 7/1991 | Dunn et al. | |
| 5,122,342 A | 6/1992 | McCulloch et al. | |
| 5,129,212 A * | 7/1992 | Duffey et al. | 53/426 |
| 5,144,146 A | 9/1992 | Wekhof | |
| 5,169,642 A | 12/1992 | Brinker et al. | |
| 5,203,385 A | 4/1993 | Waber | |
| 5,208,762 A | 5/1993 | Charhut et al. | |
| 5,229,074 A | 7/1993 | Heath et al. | |
| 5,260,020 A * | 11/1993 | Wilk et al. | 422/22 |
| 5,267,174 A | 11/1993 | Kaufman et al. | |
| 5,288,285 A | 2/1994 | Carter | |
| 5,309,959 A | 5/1994 | Shaw et al. | |
| 5,319,543 A | 6/1994 | Wilhelm | |
| 5,324,519 A | 6/1994 | Dunn et al. | |
| 5,337,919 A | 8/1994 | Spaulding et al. | |
| 5,339,421 A | 8/1994 | Housel, III | |
| 5,341,854 A | 8/1994 | Zezulka et al. | |
| 5,348,585 A | 9/1994 | Weston | |
| 5,363,885 A | 11/1994 | McConnell et al. | |
| 5,366,896 A | 11/1994 | Margrey et al. | |
| 5,411,489 A | 5/1995 | Pagay et al. | |
| 5,431,201 A | 7/1995 | Torchia et al. | |
| 5,451,528 A | 9/1995 | Raymoure et al. | |
| 5,479,969 A | 1/1996 | Hardie et al. | |
| 5,502,944 A | 4/1996 | Kraft et al. | |
| 5,522,512 A | 6/1996 | Archer et al. | |
| 5,522,804 A | 6/1996 | Lynn | |
| 5,533,606 A | 7/1996 | Yuyama | |
| 5,534,222 A | 7/1996 | Kelbrick et al. | |
| 5,573,042 A | 11/1996 | De Haen | |
| 5,597,995 A | 1/1997 | Williams et al. | |
| 5,611,051 A | 3/1997 | Pirelli | |
| 5,635,394 A | 6/1997 | Horn | |
| 5,660,305 A | 8/1997 | Lasher et al. | |
| 5,666,410 A | 9/1997 | McLane | |
| 5,680,858 A | 10/1997 | Hansen et al. | |
| 5,700,998 A | 12/1997 | Palti | |
| 5,713,485 A | 2/1998 | Liff et al. | |
| 5,713,487 A | 2/1998 | Coughlin | |
| 5,744,094 A | 4/1998 | Castberg et al. | |
| 5,768,853 A | 6/1998 | Bushnell et al. | |
| 5,769,086 A | 6/1998 | Ritchart et al. | |
| 5,786,598 A | 7/1998 | Clark et al. | |
| 5,797,515 A | 8/1998 | Liff et al. | |
| 5,798,020 A | 8/1998 | Coughlin et al. | |
| 5,805,454 A | 9/1998 | Valerino, Sr. et al. | |
| 5,812,410 A | 9/1998 | Lion et al. | |
| 5,832,447 A | 11/1998 | Rieker et al. | |
| 5,839,836 A | 11/1998 | Yuyama et al. | |
| 5,848,593 A | 12/1998 | McGrady et al. | |
| 5,884,273 A | 3/1999 | Sattizahn et al. | |
| 5,884,457 A | 3/1999 | Ortiz et al. | |
| 5,895,019 A | 4/1999 | Ibarra | |
| 5,900,211 A | 5/1999 | Dunn et al. | |
| 5,907,493 A | 5/1999 | Boyer et al. | |
| 5,911,252 A | 6/1999 | Cassel | |
| 5,912,818 A | 6/1999 | McGrady et al. | |
| 5,948,360 A | 9/1999 | Rao et al. | |
| 5,963,641 A | 10/1999 | Crandall et al. | |
| 5,971,593 A | 10/1999 | McGrady | |
| 5,993,046 A | 11/1999 | McGrady et al. | |
| 6,006,946 A | 12/1999 | Williams et al. | |
| 6,013,918 A | 1/2000 | Bushnell et al. | |
| 6,037,598 A | 3/2000 | Cicha | |
| 6,048,086 A | 4/2000 | Valerino, Sr. | |
| 6,060,022 A | 5/2000 | Pang et al. | |
| 6,068,156 A | 5/2000 | Liff et al. | |
| 6,082,987 A | 7/2000 | Su et al. | |
| 6,096,561 A | 8/2000 | Tayi | |
| 6,108,588 A | 8/2000 | McGrady | |
| 6,141,412 A | 10/2000 | Smith et al. | |
| 6,155,485 A | 12/2000 | Coughlin et al. | |
| 6,161,141 A | 12/2000 | Dillon | |
| 6,181,979 B1 | 1/2001 | Murakami | |
| 6,181,982 B1 | 1/2001 | Yuyama et al. | |
| 6,200,289 B1 | 3/2001 | Hochman et al. | |
| 6,202,004 B1 | 3/2001 | Valerino | |
| 6,202,923 B1 | 3/2001 | Boyer et al. | |
| 6,203,535 B1 | 3/2001 | Barney et al. | |
| 6,249,717 B1 | 6/2001 | Nicholson et al. | |
| 6,249,774 B1 | 6/2001 | Roden et al. | |
| 6,279,724 B1 | 8/2001 | Davis | |
| 6,318,630 B1 | 11/2001 | Coughlin et al. | |
| 6,343,690 B1 | 2/2002 | Britton et al. | |
| 6,355,024 B1 | 3/2002 | Small et al. | |
| 6,360,794 B1 | 3/2002 | Turner | |
| 6,370,841 B1 | 4/2002 | Chudy et al. | |
| RE37,829 E | 9/2002 | Charhut et al. | |
| 6,461,568 B1 | 10/2002 | Eckhardt | |
| 6,470,234 B1 | 10/2002 | McGrady | |
| 6,477,442 B1 | 11/2002 | Valerino, Sr. | |
| 6,564,121 B1 | 5/2003 | Wallace et al. | |
| 6,566,659 B1 | 5/2003 | Clark et al. | |
| 6,592,816 B1 | 7/2003 | Ebel et al. | |
| 6,599,476 B1 | 7/2003 | Watson et al. | |
| 6,604,903 B2 | 8/2003 | Osborne et al. | |
| 6,616,771 B2 | 9/2003 | Osborne et al. | |
| 6,623,455 B2 | 9/2003 | Small et al. | |
| 6,673,048 B1 | 1/2004 | Duchon et al. | |
| 6,722,404 B2 | 4/2004 | Osborne | |
| 6,735,497 B2 | 5/2004 | Wallace et al. | |
| 6,832,844 B2 | 12/2004 | Guzorek | |
| 6,847,861 B2 | 1/2005 | Lunak et al. | |
| 6,877,530 B2 | 4/2005 | Osborne et al. | |
| 6,883,681 B1 * | 4/2005 | Coughlin et al. | 221/123 |
| 6,915,823 B2 | 7/2005 | Osborne et al. | |
| 6,975,924 B2 | 12/2005 | Kircher et al. | |
| 6,976,349 B2 | 12/2005 | Baldwin et al. | |
| 6,985,870 B2 | 1/2006 | Martucci et al. | |
| 6,986,234 B2 | 1/2006 | Liedtke | |
| 6,991,002 B2 | 1/2006 | Osborne et al. | |
| 7,007,443 B2 | 3/2006 | Liedtke et al. | |
| 7,100,792 B2 | 9/2006 | Hunter et al. | |
| 7,108,679 B2 | 9/2006 | Alchas | |
| 7,117,902 B2 | 10/2006 | Osborne | |
| 7,260,447 B2 | 8/2007 | Osborne et al. | |
| 7,278,813 B2 | 10/2007 | Davies et al. | |
| 7,403,901 B1 | 7/2008 | Carley et al. | |
| 7,630,788 B1 | 12/2009 | Reese | |
| 2001/0018937 A1 | 9/2001 | Nemoto | |
| 2002/0020459 A1 | 2/2002 | Baldwin et al. | |
| 2002/0035412 A1 | 3/2002 | Kircher et al. | |
| 2002/0146343 A1 | 10/2002 | Jenkins et al. | |
| 2002/0198738 A1 | 12/2002 | Osborne | |
| 2003/0046114 A1 | 3/2003 | Davies et al. | |
| 2003/0097368 A1 | 5/2003 | Tribble et al. | |
| 2003/0147770 A1 * | 8/2003 | Brown et al. | 422/24 |
| 2003/0216831 A1 | 11/2003 | Hart et al. | |

| | | | |
|---|---|---|---|
| 2004/0028553 | A1 | 2/2004 | Panico |
| 2004/0034447 | A1 | 2/2004 | Vollm |
| 2004/0099869 | A1 | 5/2004 | Gaska et al. |
| 2004/0104243 | A1 | 6/2004 | Osborne et al. |
| 2004/0123567 | A1 | 7/2004 | McErlean et al. |
| 2004/0154690 | A1 | 8/2004 | Osborne et al. |
| 2004/0193317 | A1 | 9/2004 | Lunak et al. |
| 2004/0241041 | A1 | 12/2004 | Woodworth et al. |
| 2004/0249498 | A1 | 12/2004 | William et al. |
| 2004/0250842 | A1 | 12/2004 | Adams et al. |
| 2005/0045242 | A1 | 3/2005 | Osborne |
| 2005/0133729 | A1 | 6/2005 | Woodworth et al. |
| 2005/0224137 | A1 | 10/2005 | Tribble et al. |
| 2005/0236579 | A1 | 10/2005 | Jenkins et al. |
| 2005/0252572 | A1 | 11/2005 | Khan et al. |
| 2005/0252574 | A1 | 11/2005 | Khan et al. |
| 2005/0279419 | A1 | 12/2005 | Tribble et al. |
| 2006/0136095 | A1 | 6/2006 | Rob et al. |
| 2006/0224414 | A1 | 10/2006 | Astrup et al. |
| 2006/0225383 | A1 | 10/2006 | Cobb et al. |
| 2006/0259195 | A1 | 11/2006 | Eliuk et al. |
| 2008/0114328 | A1 | 5/2008 | Doherty |
| 2009/0067973 | A1 | 3/2009 | Eliuk et al. |
| 2009/0126825 | A1 | 5/2009 | Eliuk et al. |
| 2009/0138340 | A1 | 5/2009 | Borr et al. |
| 2010/0017031 | A1 | 1/2010 | Rob et al. |

FOREIGN PATENT DOCUMENTS

| | | |
|---|---|---|
| DE | 4 314 657 | 11/1994 |
| IT | 1 316 152 | 3/2003 |
| WO | WO 90/09776 | 9/1990 |
| WO | WO 94/04415 | 3/1994 |
| WO | WO 95/15142 | 6/1995 |
| WO | WO 97/43915 | 11/1997 |
| WO | WO 99/29412 | 6/1999 |
| WO | WO 99/29415 | 6/1999 |
| WO | WO 99/29467 | 6/1999 |
| WO | WO 00/16213 | 3/2000 |
| WO | WO 2006/069361 | 6/2006 |
| WO | WO 2006/124211 | 11/2006 |
| WO | WO2008/058280 | 5/2008 |
| WO | WO 2008/101353 | 8/2008 |
| WO | WO 2009/033283 | 3/2009 |
| WO | WO2009/033283 | 3/2009 |
| WO | WO2009/062316 | 5/2009 |

OTHER PUBLICATIONS

Re Exam Notification re Brief, Control No. 95/000,334; mailed Sep. 29, 2009 7 pages.

Re Exam Right of Appeal Notice, Control No. 95/000,333; mailed Dec. 2, 2009.

International Preliminary Report on Patentabililty, PCT/CA2008/000348, dated Sep. 3, 2009, 10 pages.

International Search Report and Written Opinion, PCT/CA2008/000348 dated Jun. 3, 2008, 10 pages.

Office Action in U.S. Appl. No. 11/316,795 notification date Dec. 29, 2008, 16 pages.

Office Action in U.S. Appl. No. 11/389,995 notification date Apr. 28, 2009, 8 pages.

Patent Owner's Entry in Reexam Control No. 95/000,333; filed Jan. 22, 2010; 32 pages.

Interview Summary in U.S. Appl. No. 11/316,795 notification date Feb. 24, 2009; 4 pages.

Reply to office action in U.S. Appl. No. 11/316,795 notification date Mar. 27, 2009; 14 pages.

Notice of Allowance in U.S. Appl. No. 11/316,795 mailing date Jun. 22, 2009; 6 pages.

Interview Summary in U.S. Appl. No. 11/389,995 notification date Jun. 17, 2009; 4 pages.

Reply to office action in U.S. Appl. No. 11/389,995 notification date Sep. 15, 2009; 14 pages.

Express Withdrawal of Appeal in Reexam Control No. 95000334; filed Oct. 29, 2009; 4 pages.

Patent Owner Petition in Reexam Control No. 95/000334; filed Nov. 10, 2009; 8 pages.

Reply to Office Action in European Application serial No. 05855521.0, filed Jan. 8, 2010, pp. 15.

U.S. Appl. No. 60/865,105, filed Nov. 9, 2006.

U.S. Appl. No. 60/891,433, filed Feb. 23, 2007.

U.S. Appl. No. 60/971,815, filed Sep. 12, 2007.

Biomedical Technology Consulting, "05BTC—Cytocare: Automatic system for the preparation of cytostatic drugs," pp. 1-22 with translation; downloaded from Internet site www.tecnomedical.com on Aug. 14, 2006.

International Search Report/Written Opinion, PCT/US2005/046978 date mailed Aug. 2, 2006, 16 pages.

Wekhof, "Basic Definitions and Data for Electron Beam Sterilization," SteriBeam Systems, GmbH, 2005, 2 pages.

Wekhof, "Disinfection with Flash Lamps," PDA Journal of Pharmaceutical Science & Technology, 2000, 54(3):264-276.

Wekhof, "Does the Engineering of the PureBright Sterilisation System Match the Pulsed Light Sterilisation Process?" Advanced Ultra-Fast Sterilisation from SteriBeam Systems GmbH, Kehl, Germany, 2001, http://www.steribeam.com/articles/WTPP-Rep/html, 6 pages.

"Industrial Automated Pulsed UV Modules," Advanced Pulsed UV and Corona Systems from SteriBeam GmbH, Kehl, Germany, http://www.steribeam.com/f-scale.puv.

Wekhof et al., "Pulsed UV Disintegration (PUVD): a new sterilization mechanism for packaging and broad medical-hospital applications," The First International Conference on Ultraviolet Technologies, Jun. 14-16, 2001, Washington, D.C., 15 pages.

Cote and Torchia, "Robotic system for i.v. antineoplastic drug preparation: Description and preliminary evaluation under simulated conditions" Am. J. Hosp. Pharm., 1989, 46:2286-2293.

"Two UV-flashlamps R&D/Labor Automated System," Advanced Pulsed UV and Corona Systems From SteriBeam GmbH, Kehl, Germany, http://www.steribeam.com/xe-labor-wt.html.

EPO Extended European Search Report for EP Application No. 06751430.7 (PCT/US2006/015731), mailed Sep. 14, 2009, 7 pages.

"Aseptic Technique Process and End-product Evaluation," Department of Pharmacy Policy, 1994, University of Kentucky Hospital, Chandler Medical Center, 4 pages.

"BD Helping all people live health lives Prefilled. Proven. Preferred.," BD Product Literature, BD, 2000.

"Welcome to the Future. The Robotic IV Admixture System: The established wave of the future with real bottom line savings." Robotic IV Admixture System; Canada, 1992.

"Dose Systems." Pharmaceutical Journal; pp. 757, vol. 254, No. 6843; Jun. 3, 1995.

International Search Report and Written Opinion, PCT/CA2008/001613 dated Sep. 12, 2008, 10 pages.

International Search Report and Written Opinion, PCT/US06/15731 dated Jul. 29, 2008, 10 pages.

International Search Report and Written Opinion, PCT/US07/84332 dated Jul. 1, 2008, 11 pages.

International Search Report and Written Opinion, PCT/US2005/046978 dated Aug. 2, 2006, 16 pages.

International Search Report and Written Opinion, PCT/CA2008/002027 dated Feb. 25, 2009, 12 pages.

'Definition of "cannulal", Webster's Third New International Dictionary, Unabridged. Copyright 1993 Merriam-Webster, Incorporated.

Kohler, et al. "Standardizing the expression and nomenclature of cancer treatment regiments," Am J Health-Svst Pharm: 1998; 55: 137-144.

Office Action in Re Exam Control No. 95/000,333; mailed Mar. 7, 2008; 36 pages.

Office Action in Re Exam Control No. 95/000,333; mailed May 5, 2009; 36 pages.

Office Action in Re Exam Control No. 95/000,334; mailed Feb. 27, 2008; 17 pages.

Office Action in Re Exam Control No. 95/000,335; mailed Mar. 7, 2008; 16 pages.

Office Action in Re Exam Control No. 95/000,336; mailed Mar. 11, 2008; 36 pages.

Office Action in Re Exam Control No. 95/000,336; mailed Oct. 15, 2008; 18 pages.

Office Action in Re Exam Control No. 95/000,340; mailed Mar. 21, 2008; 41 pages.

Office Action in Re Exam Control No. 95/000,340; mailed Mar. 30, 2009; 65 pages.
Office Action in Re Exam Control No. 95/000,342; mailed Mar. 11, 2008; 18 pages.
Office Action in Re Exam Control No. 95/000,342; mailed Oct. 15, 2008; 28 pages.
Office Action in Re Exam Control No. 95/000,345; mailed Apr. 23, 2008; 110 pages.
Office Action in Re Exam Control No. 95/000,345; mailed Mar. 30, 2009; 65 pages.
Patent Owner's Response in Re Exam Control No. 95/000,333; filed Jun. 12, 2008, 11 pages.
Patent Owner's Response in Re Exam Control No. 95/000,333; filed Jun. 7, 2008, 38 pages.
Patent Owner's Response in Re Exam Control No. 95/000,333; filed Jun. 16, 2009, 16 pages.
Patent Owner's Response in Re Exam Control No. 95/000,335; filed Jun. 7, 2008, 34 pages.
Patent Owner's Response in Re Exam Control No. 95/000,336; filed Nov. 14, 2008, 35 pages.
Patent Owner's Response in Re Exam Control No. 95/000,336; filed Jun. 12, 2008, 13 pages.
Patent Owner's Response in Re Exam Control No. 95/000,336; filed Jun. 7, 2008, 44 pages.
Patent Owner's Response in Re Exam Control No. 95/000,340; filed Jun. 12, 2008, 10 pages.
Patent Owner's Response in Re Exam Control No. 95/000,340; filed May 20, 2008, 39 pages.
Patent Owner's Response in Re Exam Control No. 95/000,342; filed Jun. 7, 2008,33 pages.
Patent Owner's Response in Re Exam Control No. 95/000,342; filed Nov. 13, 2008, 14 pages.
Patent Owner's Response in Re Exam Control No. 95/000,345; filed Jun. 23, 2008, 32 pages.
Patent Owner's Response in Re Exam Control No. 95/000,345; filed Apr. 29, 2009, 8 pages.
Request for InterPartes Reexamination in Reexam Control No. 95/000,333; filed Jan. 11, 2008; 39 pages.
Request for InterPartes Reexamination in Reexam Control No. 95/000,334; filed Jan. 11, 2008; 54 pages.
Request for InterPartes Reexamination in Reexam Control No. 95/000,335; filed Jan. 11, 2008; 73 pages.
Request for InterPartes Reexamination in Reexam Control No. 95/000,336; filed Jan. 11, 2008; 97 pages.
Request for InterPartes Reexamination in Reexam Control No. 95/000,340; filed Jan. 30, 2008; 33 pages.
Request for InterPartes Reexamination in Reexam Control No. 95/000,342; filed Feb. 1, 2008; 27 pages.
Request for InterPartes Reexamination in Reexam Control No. 95/000,345; filed Feb. 11, 2008; 32 pages.
Third Party Comments on Patent Owner Response in Reexam Control No. 95/000,333; filed Jul. 7, 2008; 29 pages.
Third Party Comments on Patent Owner Response in Reexam Control No. 95/000,335; filed Jul. 7, 2008; 18 pages.
Third Party Comments on Patent Owner Response in Reexam Control No. 95/000,336; filed Dec. 15, 2008; 7 pages.
Third Party Comments on Patent Owner Response in Reexam Control No. 95/000,336; filed Jul. 7, 2008; 22 pages.
Third Party Comments on Patent Owner Response in Reexam Control No. 95/000,340; filed Jun. 19, 2008; 19 pages.
Third Party Comments on Patent Owner Response in Reexam Control No. 95/000,342; filed Dec. 15, 2008; 7 pages.
Third Party Comments on Patent Owner Response in Reexam Control No. 95/000,342; filed Jul. 7, 2008; 28 pages.
Third Party Comments on Patent Owner Response in Reexam Control No. 95/000,345; filed Jul. 23, 2008; 16 pages.
Third Party Comments on Patent Owner Response in Reexam Control No. 95/000,333; filed Jul. 16, 2009; 9 pages.
Office Action in Re Exam Control No. 95/000,345; mailed Jul. 2, 2009 73 pages.
Office Action in Re Exam Control No. 95/000,340; mailed Jul. 20, 2009, 8 pages.

* cited by examiner

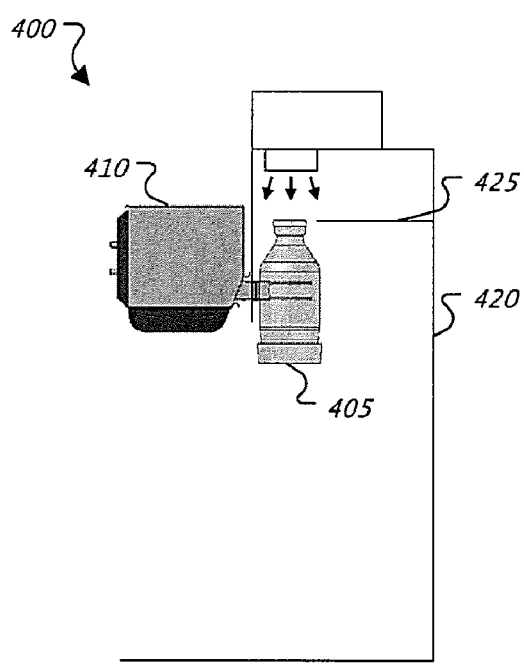
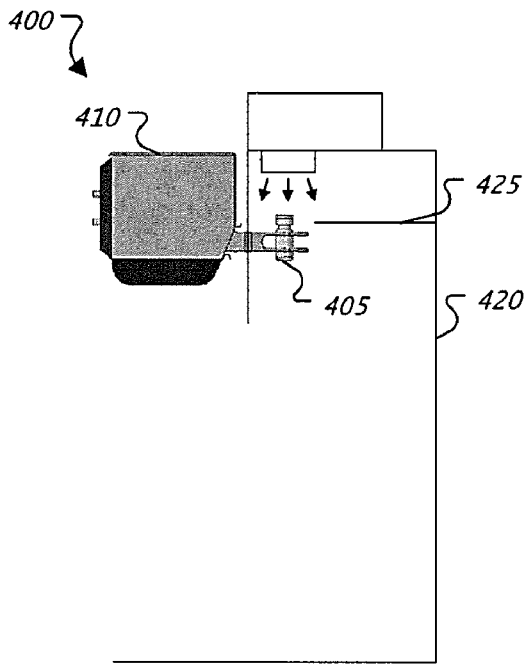
FIG. 4A
FIG. 4B
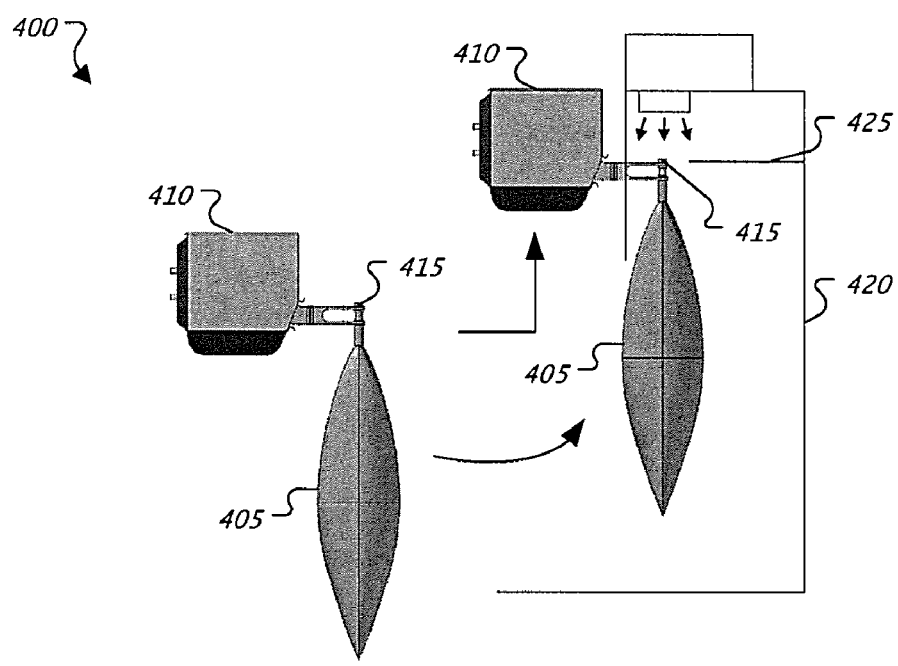
FIG. 4C

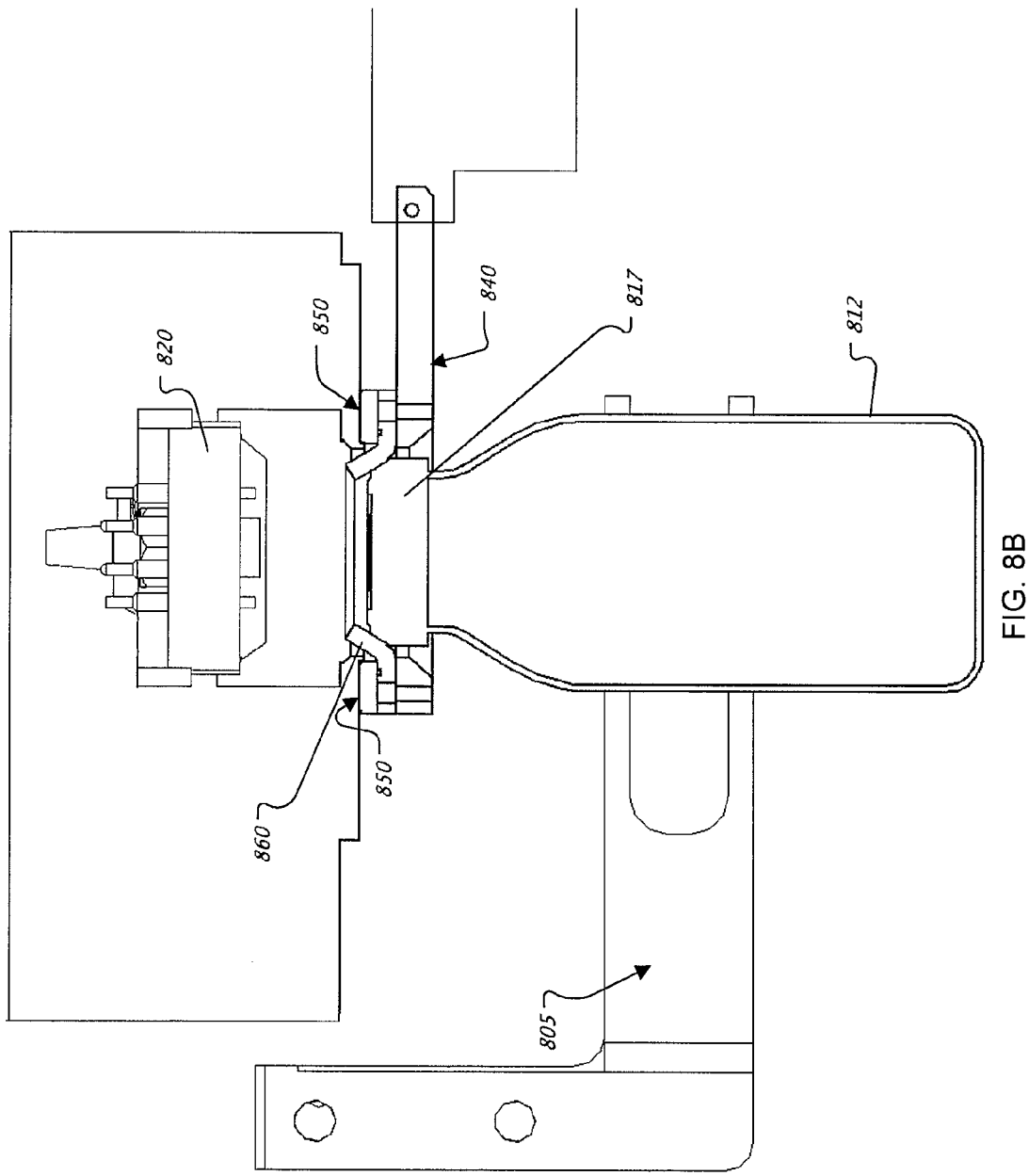

ULTRAVIOLET SANITIZATION IN PHARMACY ENVIRONMENTS

CROSS REFERENCE TO RELATED APPLICATIONS

This application claims priority under 35 USC §119(e) to U.S. Provisional Patent Application Ser. No. 60/891,433, entitled "Ultraviolet Disinfection In Pharmacy Environments," filed on Feb. 23, 2007, by Mlodzinski et al. This application also claims priority under 35 USC §119(e) to U.S. Provisional Patent Application Ser. No. 60/988,660, entitled "Method and Apparatus for Automated Fluid Transfer Operations," filed on Nov. 16, 2007, by Eliuk et al. This application also claims priority under 35 USC §119(e) to U.S. Provisional Patent Application Ser. No. 60/971,815, entitled "Gripper Device," filed on Sep. 12, 2007, by Eliuk et al. In addition, this application is a continuation-in-part and claims priority under 35 USC §120 to U.S. patent application Ser. No. 11/316,795, entitled "Automated Pharmacy Admixture System," and filed on Dec. 22, 2005, by Rob et al. This application is also a continuation-in-part and claims priority under 35 USC §120 to U.S. patent application Ser. No. 11/389,995, entitled "Automated Pharmacy Admixture System," and filed on Mar. 27, 2006, by Eliuk et al. This application further is a continuation-in-part and claims priority under 35 USC §120 to U.S. patent application Ser. No. 11/937,846, entitled "Control of Fluid Transfer Operations," and filed on Nov. 9, 2007, by Doherty et al. The entire disclosures of each of the aforementioned documents are incorporated herein by reference.

TECHNICAL FIELD

Various embodiments relate to handling medical containers such as syringes, vials, and IV bags.

BACKGROUND

Many medications are delivered to a patient from an intravenous (IV) bag into which a quantity of a medication is introduced. Sometimes, the medication may be an admixture with a diluent. In some cases, the IV bag contains only the medication and diluent. In other cases, the IV bag may also contain a carrier or other material to be infused into the patient simultaneously with the medication. Medication can also be delivered to a patient using a syringe.

Medication is often supplied, for example, in powder form in a medication container or in a vial. A diluent liquid may be supplied for making an admixture with the medication in a separate or diluent container or vial. A pharmacist may mix a certain amount of medication (e.g., which may be in dry form such as a powder) with a particular amount of a diluent according to a prescription. The admixture may then be delivered to a patient.

One function of the pharmacist is to prepare a dispensing container, such as an IV bag or a syringe, that contains a proper amount of diluent and medication according to the prescription for that patient. Some prescriptions (e.g., insulin) may be prepared to suit a large number of certain types of patients (e.g., diabetics). In such cases, a number of similar IV bags containing similar medication can be prepared in a batch, although volumes of each dose may vary, for example. Other prescriptions, such as those involving chemotherapy drugs, may require very accurate and careful control of diluent and medication to satisfy a prescription that is tailored to the needs of an individual patient.

The preparation of a prescription in a syringe or an IV bag may involve, for example, transferring fluids, such as medication or diluent, among vials, syringes, and/or IV bags. IV bags are typically flexible, and may readily change shape as the volume of fluid they contain changes. IV bags, vials, and syringes are commercially available in a range of sizes, shapes, and designs.

SUMMARY

Systems and methods to reduce bioburden on at least a portion of a fluid transfer port include supplying a dose of radiation to the fluid transfer port that is in optical communication with at least one source of radiation. In an illustrative example, a medical container, such as a vial or IV bag, receives a dose of ultraviolet (UV) energy substantially at a predetermined region of a fluid transfer site. In some examples, such a sanitization process may precede a fluid transfer operation in which a fluid is transferred into or out of the medical container by passing through the sanitized region. Such fluid transfers may be used in automated or semi-automated pharmaceutical processes, such as drug reconstitution. Various embodiments may further include one or more seal assemblies, each seal assembly having an aperture through which the radiation dose is supplied from the source to a controlled region on the fluid transfer port.

In one embodiment, an Automated Pharmacy Admixture System (APAS) may include an automated system to transport medical containers such as bags, vials, or syringes in a compounding chamber that may be regulated to a pressure above or below atmospheric pressure. In one implementation, the automated transportation system is configured to grasp and convey syringes, IV bags, and vials of varying shapes and sizes from a storage system in an adjacent chamber that may be regulated at a pressure above or below atmospheric pressure. Various embodiments may include a controller adapted to actuate the automated transportation system to bring a fill port of an IV bag, vial, or syringe into register with a filling port at a fluid transfer station in the chamber. One implementation includes a sanitization system that can substantially sanitize a bung on a fill port of a vial or IV bag in preparation for transport to the fluid transfer station. A port sanitization system (PSS) may be used in the sanitization of vial and bag ports in an IV admixture compounding application. The PSS system may be a stand-alone or table top system, or may be adapted for integration into an APAS cell. The PSS may include one or more radiation (e.g., UV) sources; one or more mechanisms for holding a medical container (e.g., drug vial, IV bag and syringe); one or more mechanisms for radiation sealing or containment; one or more cooling, purging and/or venting systems; a control and monitoring system; and interlocks and/or safety mechanisms.

The PSS may utilize a single centralized UV source or multiple distributed UV sources. The UV source(s) can deliver UV radiation in a pulsed and/or constant wave form and by continuous emission, intermittent emission or pulsed emission. The UV source(s) can deliver a predetermined dose in a fixed or variable profile based on the target biocontaminant(s). To reduce transmission loss, at least one optical conduit (e.g., light pipe, optical fiber, and optical waveguide) may be used to transmit the UV radiation from the UV source(s) to the object(s) to be sanitized.

The PSS may include one or more aperture assembly for sealing or containing the UV radiation. The sealing assembly can be designed such that in operation the sealing assembly does not touch the area(s) to be sanitized. In some embodiments, the sealing aperture assembly includes at least one baffle that is configured to form one or more apertures. In some embodiments, the sealing aperture assembly includes a gasket that is formed around an aperture. A pressure chamber may be used to engage a medical container with the sealing assembly by substantially forming a light seal between them. In some embodiments, the sealing aperture assembly includes a concave receptacle with an aperture. In some embodiments, multiple sealing aperture assemblies are used to cover medical containers with different shapes and sizes.

The PSS may incorporate a controller that can determine which radiation seal assembly should be used based on the size and/or shape of the medical container to be sanitized.

The PSS may also include an actuator that can move various components (e.g., the medical container, the apparatus for holding the medical container, the radiation sealing assembly, and the UV source) either individually or in concert to bring the portion of the fluid transfer port to be sanitized into optical communication with the UV source through the aperture of the radiation seal assembly.

Various embodiments may provide one or more of the following advantages. The APAS may compound toxic and/or volatile substances, such as those used for chemotherapy, in a substantially aseptic chamber at pressure below ambient pressure to substantially avoid unintentional escape of the substances outside of the chamber. Also, the APAS may be programmed to select medical containers, such as IV bags, syringes, and/or vials, according to site-specific (e.g., hospital) protocols for containers for particular drug orders. Additionally, medical items, including IV bag and vial bung ports, may be positioned to receive a sanitizing dose of ultraviolet, which can effectively decrease bioburden (e.g., viruses, bacteria, mold, etc.). Further advantages may include reduction or elimination of sanitizing consumables, and a significantly reduced risk of explosive fumes (in the enclosed cell context) associated with some consumable sanitizers.

The details of one or more embodiments are set forth in the accompanying drawings and the description below. Other features, objects, and advantages will be apparent from the description and drawings, and from the claims.

DESCRIPTION OF DRAWINGS

FIGS. 4A-4C show cross-sectional views of an illustrative PSS that accepts variously sized objects to be sanitized in an APAS cell.

FIGS. 8A and 8B shows an exemplary IV bag and drug vial sanitization, respectively.

DETAILED DESCRIPTION OF ILLUSTRATIVE EMBODIMENTS

An Automated Pharmacy Admixture System (APAS) may include a manipulator that transports medical containers such as bags, vials, or syringes about a substantially aseptic admixing chamber. In some examples, the chamber includes a number of processing stations at which the medical containers can be processed to perform reconstitution for prescription medication doses. In particular examples, such processing stations may include apparatus to substantially sanitize, disinfect, and/or sterilize portions of the medical containers prior to performing a fluid transfer operation.

In an example implementation, a gripper assembly is configured to substantially universally grasp and retain syringes, IV bags, and vials of varying shapes and sizes. In an illustrative embodiment, a gripping device may include claws configured to grasp a plurality of different types of IV bags, each type having a different fill port configuration. Embodiments may include a controller adapted to actuate a transport assembly to place a fill port of the bag, vial or syringe into register with a filling port such as a cannula located at a filling station, or be equipped with carousel transport systems that are adapted to convey bags, vials, and syringes to the admixture system and deliver constituted medications in bags, vials or syringes to an egress area.

Figure 1:
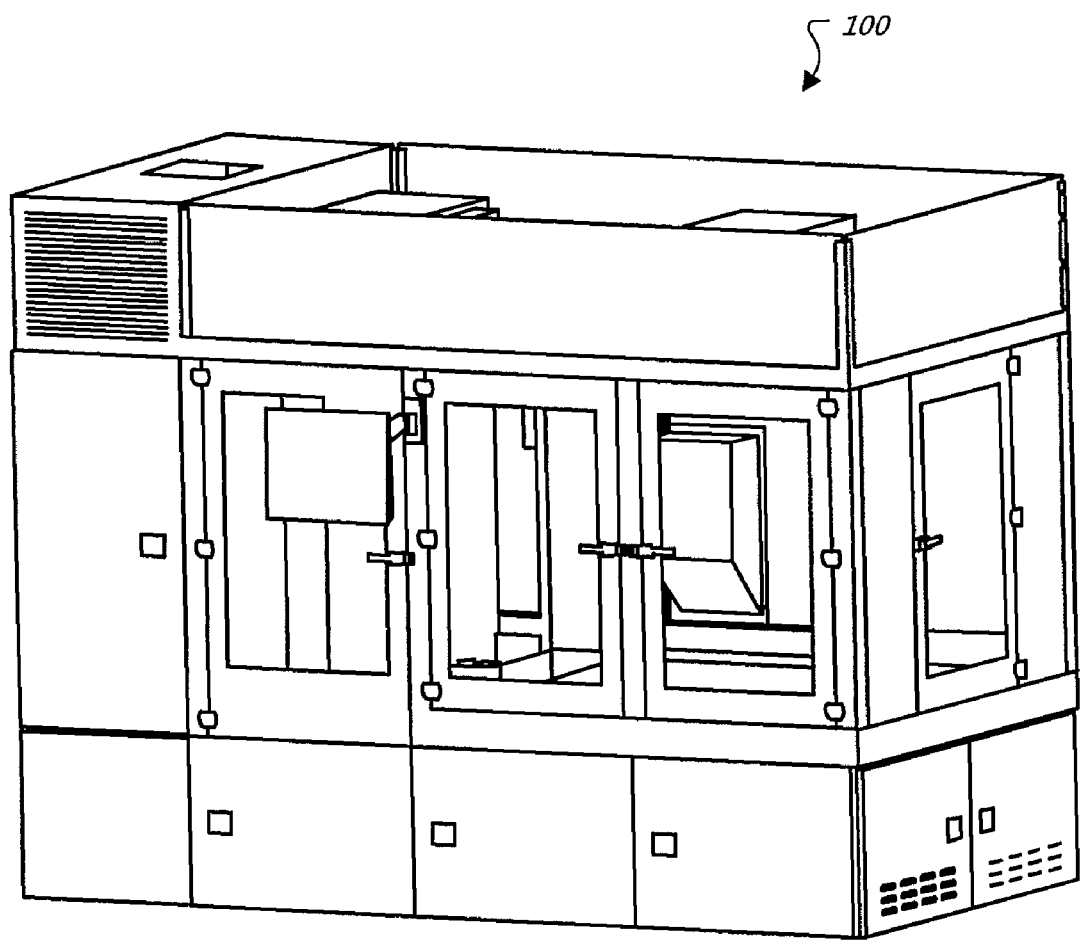
FIG. 1 shows an illustrative Automated Pharmacy Admixture System (APAS) cell.

FIG. 1 shows an illustrative Automated Pharmacy Admixture System (APAS) cell device 100 for use within a hospital pharmacy environment. The APAS cell 100 may autonomously admix contents of syringes and IV bags using automation technologies. For example, embodiments of the APAS cell 100 may perform one or more operations that might otherwise be performed by pharmacy staff within a laminar airflow hood. The APAS cell 100 includes a robotic cell that automates the compounding and dispensing of drug doses into IV bags and/or syringes, such as those that may be prepared in hospital pharmacies. The robotic cell may use a syringe-based fluid transfer process, and may employ a robotic manipulator (e.g., a multiple degree of freedom arm) for moving drug vials, syringes, and IV bags through the cell as the medications are processed.

Figure 2:
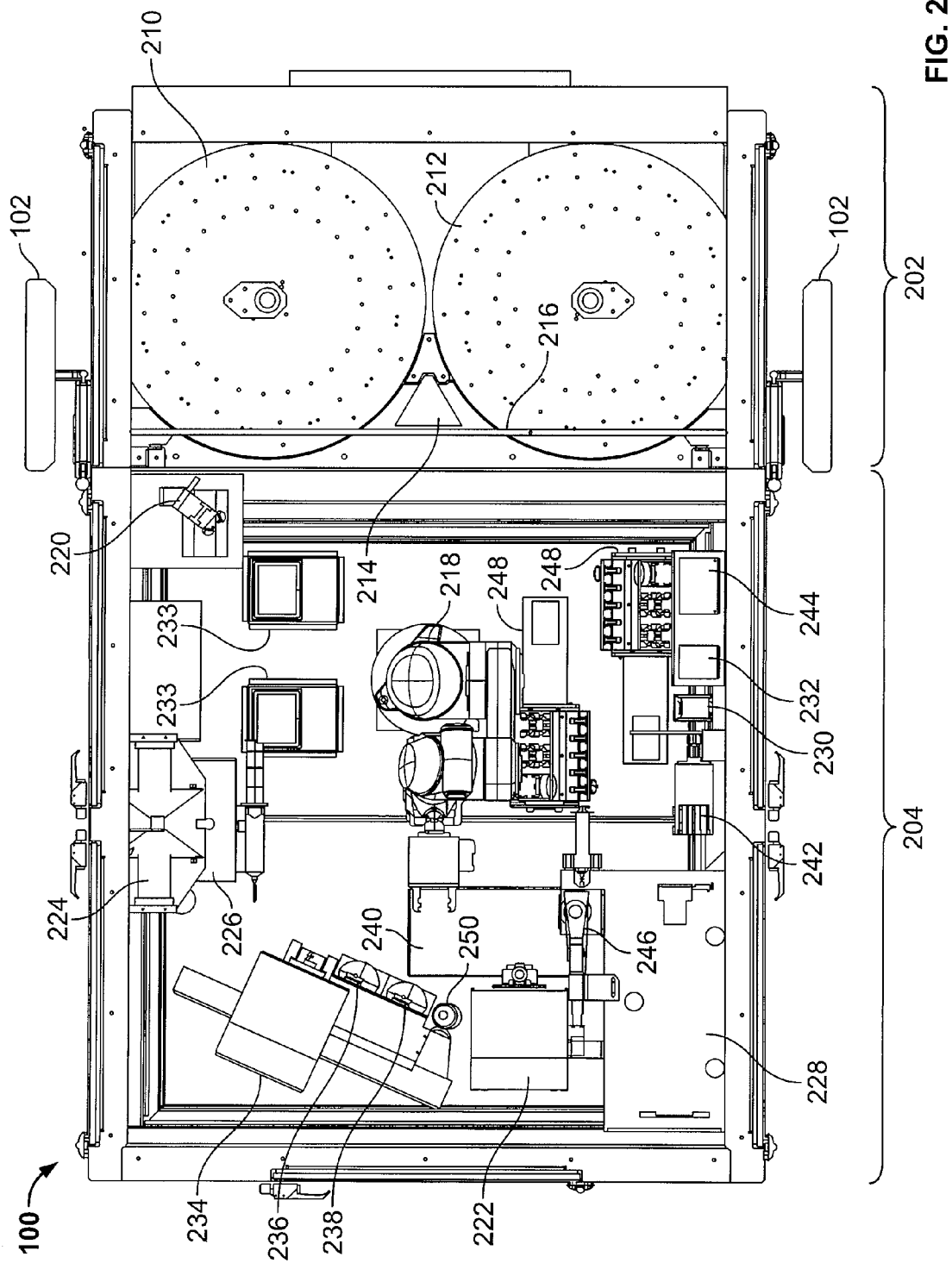
FIG. 2 shows a top cut-away view of the APAS cell of FIG. 1.

FIG. 2 shows an illustrative top cut-away view of the APAS cell of FIG. 1. The APAS cell 100 includes two chambers. An inventory chamber 202 is used as an inventory loading area, which can be accessed by an operator to load the APAS cell 100 through a loading door (not shown). In some embodiments, the inventory chamber 202 provides a substantially aseptic environment, which may be an ISO Class 5 environment that complies with clean room standards. A processing chamber 204 includes the compounding area in which the admixture and/or compounding processes may occur. In some embodiments, the processing chamber 204 provides a substantially aseptic environment, which may be an ISO Class 5 environment that complies with clean room standards. Mounted on the exterior of the APAS cell 100 are two of the monitors 102, which may serve as input/output devices.

The inventory chamber 202 includes two inventory rack carousels 210 and 212 and a temporary inventory rack 214. The temporary inventory rack 214 may be used to locate in-process drug vials that contain enough material to provide multiple doses. Each inventory rack carousel 210 or 212 may support multiple inventory racks (not shown). In some applications, an operator may remove one or more racks from the carousels 210, 212 and replace them with racks loaded with inventory. The racks may be loaded onto the carousels 210, 212 according to a load map, which may be generated by the operator for submission to the APAS cell 100, or generated by the APAS cell 100 and communicated to the operator. The chambers 202, 204 are substantially separated by a dividing wall 216.

The processing chamber 204 includes a multiple degree of freedom robotic arm 218, and the robotic arm 218 further includes a gripper that can be used, for example, to pick items from a pocket on a rack or to grasp items within the APAS cell 100 for manipulation. The robotic arm 218 may respond to command signals from a controller (not shown) to pick up, manipulate, or reposition inventory items within the processing chamber 204, and in or around the carousels 210, 212. The robotic arm 218 may manipulate inventory items, for example, by picking a vial, IV bag, or syringe from a rack of the carousels 210, 212 in the inventory chamber 202, and moving the item to a station in the processing chamber 204 for use in compound preparation. In some examples, the robotic arm 218 may manipulate inventory items on the carousels 210, 212 through access port (not shown) in the dividing wall 216. The dividing wall 216 may be substantially sealed so that a substantially aseptic environment may be maintained for compounding processes in the processing chamber 204.

According to an illustrative example, an incoming drug order from a remote user station (not shown) involves a batch production order for syringes to be charged with individual doses of a drug that is reconstituted from a drug provided in one or more vials. The operator, for example, may preload the drug into the APAS cell 100 during a loading process by loading the carousel 210 with inventory racks of the drug vials, and by interfacing with the APAS cell 100 using the input/output device 102 to initiate, monitor, and/or control the loading process. As the APAS cell 100 is processing a previous order, the operator may load the carousel 212 with inventory racks of syringes, drug vials, and IV bags for the next batch production order while the APAS cell 100 is operating the carousel 210. Once the loading process is complete, the operator may submit the batch production process, which may begin immediately, or after other processing is completed.

To execute the batch production, in this example, the robotic arm 218 may pick a syringe from a pocket in a rack in carousel 210. The syringe in the carousel may have a needle and a needle cap. The needle cap is removed for processing in the APAS cell 100. The robotic arm 218 may convey the syringe to a decapper/deneedler station 220 where the needle cap is removed from the syringe/needle assembly to expose the needle. The robotic arm 218 moves the syringe to a scale station 226 where the syringe is weighed to determine its empty weight. The robotic arm 218 may transfer the syringe to a needle-up syringe manipulator 222 where a dose of the drug is drawn from a vial, which was previously placed there by the robotic arm 218 after one or more verification operations (e.g. weighing, bar code scanning, and/or machine vision recognition techniques). The robotic arm 218 moves the syringe to the decapper/deneedler station 220 where the needle is removed from the syringe and disposed of into a sharps container (not shown). The robotic arm 218 then moves the syringe to a syringe capper station 224, where the needleless syringe is capped. The robotic arm 218 moves the syringe to a scale station 226 where the syringe is weighed to confirm the predetermined dose programmed into the APAS cell. The robotic arm 218 then moves the syringe to a printer and labeling station 228 to receive a computer readable identification (ID) label that is printed and applied to the syringe. This label may have a bar code or other computer readable code printed on it which may contain, for example, patient information, the name of the drug in the syringe, the amount of the dose, as well as date and/or lot code information for the inputs. The robotic arm 218 then moves the syringe to an output scanner station 230 where the information on the ID label is read by the scanner to verify that the label is readable. The APAS cell 100 may report back to the remote user station using a local communication network, for use in operations planning. The syringe is then taken by the robotic arm 218 and dropped into the syringe discharge chute 232 where it is available to the pharmacy technician, for example, to be placed in inventory within the hospital pharmacy. As the process continues, there may be times during the drug order process where the robotic arm 218 removes an empty vial from the needle-up syringe manipulator 222 and places it into a waste chute 233.

In another illustrative example, a syringe may be used both as an input containing a fluid (e.g., diluent or known drug compound) to be admixed in a compounding process, and as an output containing a prepared dose suitable for delivery to a patient. Such a syringe may be needed to fulfill a special reconstitution order programmed into the APAS cell 100 via the input/output capabilities of the monitor 102, for example. In another example, the order may be a stat order, which may be received from a hospital interface. In this example, the operator performs in situ loading by placing the syringes to be used for both reconstitution and dosing in pockets on a rack already located on the carousel 210. The operator enters the reconstitution order into the APAS cell 100. The robotic arm 218 picks the selected syringe from a pocket in the rack in the carousel 210 and moves it to the decapper/deneedler station 220, where the needle cap is removed from the syringe/needle combination, thereby exposing the needle. The syringe is then transferred by the robotic arm 218 to a needle-down syringe manipulator 234. At the station 234, diluent is drawn into the syringe from a diluent supply IV bag 236 previously placed there by the robotic arm 218. The diluent supply 236 may be contained in an IV bag which is hung on the needle-down syringe manipulator 234 by a clip (not shown). An air extraction process may be performed to prime the IV bag, if needed. The syringe then punctures the membrane of the diluent port 238 in a needle-down orientation. The syringe is actuated to remove, for example, a predetermined amount of the diluent from the IV bag. The needle-down syringe manipulator 234 then moves a reconstitution vial 250, placed there previously by the robotic arm 218, under the syringe. The diluent in the syringe is transferred to the vial for reconstitution with the vial contents. The robotic arm 218 then moves the vial to a mixer 248 for shaking according to a mixing profile. The robotic arm 218 then moves the vial to the needle-up syringe manipulator 222 where the appropriate amount of the reconstituted drug is drawn from the vial into an "output" syringe that was previously conveyed there by the robotic arm 218.

In another embodiment, the APAS cell 100 may receive a production order to prepare compounds that may involve IV bags as input inventory items or as outputs. In some examples, an IV bag may be selected as a diluent source for reconstitution in a drug order to be output into another medical container. In other examples, the selected IV bag may be used for output after preparation of the drug order is completed. Some IV bags may be placed on the carousels 210, 212 and used as an input that may be at least partially filled with a diluent that may be used to reconstitute drugs. The reconstituted drugs may be output in the form of charged syringes or IV bags. The operator loads racks of syringes and IV bags into the carousel 210 for use in the production order. During the production order, the robotic arm 218 picks an IV bag from a rack on the carousel 210 and moves it to the scale and bag ID station 226. At this station, the IV bag is identified by bar code or pattern matching and its weight is recorded. This may be done, for example, as an error check, and/or to positively identify the type and/or volume of diluent being used for reconstitution. If the IV bag is selected as a diluent source, then the bag may be weighed before use to confirm the presence of the diluent in the IV bag. If the IV bag is selected for output, it may be weighed multiple times, such as before, during, and/or after each fluid transfer step, for example. As a post-transfer verification step, the weight may be re-checked after fluid transfer operations have occurred to determine if the change in weight is within an expected range. Such checks may detect, for example, leaks, spills, overfills, or material input errors. In this example, the robotic arm 218 moves the IV bag to a port cleaner station 240 where a ultraviolet (UV) light or other sanitizing process may be used to substantially sterilize, disinfect or sanitize at least a portion of the IV bag port. The robotic arm 218 moves the IV bag to the needle-up syringe manipulator 222 where a pre-filled syringe has been loaded. The IV bag may be inverted so that the fill port is oriented downwardly for the fill process. The contents of the syringe may then be injected into the IV bag. The robotic arm 218 then conveys the IV bag to the scale station 226 where the IV bag is weighed to confirm the predetermined dose programmed into the APAS cell 100. The robotic arm 218 then moves the IV bag to a bag labeler tray station 242 where a label printed by the printer and labeling station 228 is applied to the IV bag. The robotic arm 218 may move the IV bag to the output scanner station 230, where the information on the ID label is read by the scanner to verify that the label is readable. One or more further verification checks may be performed. The IV bag is then taken by the robotic arm 218 and dropped into the IV bag discharge chute 244 where it is available to the pharmacy technician, for example, to be placed in inventory within the hospital pharmacy.

In another embodiment, a vial (or other medical item or container) may be prepared for reconstitution. During the performing of this process by the APAS cell 100, the vial may be identified at a vial ID station where, for example, a bar coded label on the vial may be read by a scanner and/or image hardware in combination with image processing software. The captured information may be processed to identify the contents of the vial and correlate it to what is expected. In some implementations, as an alternative to or in combination with bar code scanning, the APAS cell 100 may employ pattern matching on the vial using optical scanning techniques. Also, in the reconstitution process, vial mixers 248 may be used to mix the vial contents with the diluent before using it for dosing.

In some embodiments, the robotic manipulator may include apparatus for reading machine readable indicia in the APAS, including the compounding chamber and/or the storage chamber. For example, the manipulator may include a fiber optic camera for taking images that can be processed to compare to stored image information (e.g., bitmaps). In other examples, the reading apparatus may include optical scanning (e.g., bar code) or RFID (radio frequency identification). Some embodiments may transmit image information wirelessly (e.g., using infrared or RF (radio frequency) transmissions) to a receiver coupled to the APAS. Such a receiver may be located inside or outside the chamber with the robotic manipulator. Such a reader may be used to read machine readable indicia at various locations in and around the compounding chamber, including through windows and on portions of the storage carousels that are exposed to the compounding chamber.

In the embodiments described here, a UV port sanitization system (PSS) is used in the sanitization of vial and bag ports in an IV admixture compounding application. Variants of the system described here may also include sanitization of syringe bodies. The system may be part of an APAS cell or used as a stand alone device. Examples of an APAS system are described in further detail, for example, in U.S. patent application Ser. No. 11/316,795, entitled "Automated Pharmacy Admixture System," and filed on Dec. 22, 2005, and U.S. patent application Ser. No. 11/389,995, entitled "Automated Pharmacy Admixture System," and filed on Mar. 27, 2006, the contents of each of which are incorporated herein by reference.

In general, operations to sanitize an object may refer to operations to reduce the bioburden on the object to be sanitized. In some applications, a sanitizing operation may be intended to reduce active (e.g., living) bioburden to some degree. In some embodiments, the disclosed sanitization of an object may substantially disinfect at least a portion of the object. In some other embodiments, the disclosed sanitization of an object may substantially sterilize at least a portion of the object. Exemplary desired bioburden inactivation is greater than or equal to a 6 log reduction, but could vary slightly from this, depending on the target organism. In some embodiments, at least 99.9999%, 99.99%, 99%, 95%, 90%, 80%, 75%, 70%, 60%, or at least about 50% of a particular biocontaminant may be killed or incapacitated. In some embodiments, between about 1 and 100% of a particular biocontaminant may be inactivated.

In an exemplary embodiment, the mechanism of sanitizing the target object may be through the exposure of ultraviolet radiation. This exposure may be delivered in, among other methods, a pulsed and/or constant wave form. In some embodiments, the dose of ultraviolet radiation may include one or more pulses. In other embodiments, the dose may include a timed exposure at a controlled intensity. For example, the intensity may be controlled by modulation of current and/or voltage applied to the radiation source to substantially achieve the controlled radiation level, which may increase, decrease, and/or remain substantially constant during the dose time period. In some embodiments, a controller may achieve time-varying or constant radiation level by modulation of optical path's transmission characteristics, such as by selecting which of a number of optical paths to use to couple the radiation from the source to the target region on the fill port, and/or by modulating characteristics of the optical coupling (e.g., filtering) to couple more or less radiation from the source to the target. The radiation subjected to the target is known as the delivered dose. The dose includes an accumulated exposure value. In an illustrative example, a desired dose is one that is predetermined based on, for example, a desired accumulated exposure value at a specific energy density selected to be sufficient to inactivate one or more types of biocontaminants to a selected degree. In general, sanitization may involve, for example, reducing the number of viable microorganisms present in a sample.

Biocontaminants, known as the bioburden, may include, but are not limited to, viruses, bacteria, molds, protozoa and yeasts, for example. In a range of examples, ultraviolet radiation may be used to kill one or more types of the biocontaminants on, around, or within portions of an I.V. bag, syringe and/or vial, such as around the fill port of such I.V. bag, syringe and/or vial. In some cases for example, such bioburden may be found in environments such as medical clinics, hospitals, hospital pharmacies, research laboratories, or other facilities in which pharmaceuticals may be packaged, prepared, stored, transported, or otherwise handled. Some embodiments may be beneficially applied to provide or enhance sanitization of vials, syringes, packaging (e.g., I.V. bags), tubing, access ports, and/or associated equipment (e.g., handling equipment, including robotic manipulators), fluids (e.g., water), or other materials that may come into proximity and/or contact with objects for which sanitization may be a concern. Some applications may relate to the preparation of pharmaceutical and/or medical devices, such as delivery systems for providing parental nutrition or insulin to patients, for example.

In various embodiments, the UV port sanitization system (PSS) may include one or more of the following components: one or more UV sources; one or more vial, syringe, and/or bag port holding systems or methods; one or more systems or methods for appropriate sealing or containment of UV for both drug/fluid and/or user protection; one or more cooling, purging and/or venting systems; a control and monitoring system; and interlocks and/or safety mechanisms.

In various examples, some embodiments of the PSS may include a single centralized UV source with selectable masks or apertures for the variety of vials and bags. Some embodiments may also utilize multiple distributed sources that can be conveniently located (e.g., for replacement, maintenance), or combined with other subsystems or functions in the APAS cell context. In the example described here, the amount of UV time exposure required for sanitization is a function of the energy level received by the target at the required frequency spectrum. However, a predetermined exposure time for a dose may be based on other criteria. Both fixed and variable profiles may be executed at various levels of intensity, number, spacing, and timing. The outputs of UV sources may decay over time. Calibration and/or closed-loop control may be implemented by a processor, such as on a programmable logic controller or an embedded controller, to compensate such decay to maintain desired profiles (e.g., a predetermined accumulated dose of radiation).

In some embodiments that have multiple UV sources, the PSS may include apparatus to focus or direct radiation supplied from each of the UV sources onto one or more selected regions or spots, or combine their output patterns using offsets to provide the desired illumination pattern at the fill port of a target. UV sources may have non-uniform output patterns. By changing pattern centerlines, an aggregate output energy pattern that meets desired requirements can be generated. One example is to have 3 UV sources combined in such a manner as to provide a nearly uniform energy output over a much wider range than could be achieved with focusing the 3 UV sources onto a single spot.

A UV source may include, for example, flash bulbs to produce very high peak energy levels, on the order of 1 $J/cm^2$, or 10 $J/cm^2$, or 30 $J/cm^2$ in the UV-C band, which may include, but are not limited to, between 100 nm and 280 nm. In some examples, these are provided in very short bursts ranging from less than 1 ns to 100 ms at frequencies from about 0.01 Hz to about 1 kHz. Some pulsed bulbs may generate a wide band spectrum. In some embodiments, the UV light output may include a wider spectrum of radiation. For example, the pulsed UV light may include energy content in the UV-A, UV-B, and UV-C ranges, and may include some energy content at wavelengths shorter and/or longer than UV wavelengths, e.g., IR or visible light.

UV sources such as mercury vapor lamps, metal halide lamps and other constant wave sources generally provide energies in the range of about 1 $mJ/cm^2$ to 400 $mJ/cm^2$ in the UV-C band, or more. Packaged either singly or with multiple source packages to increase total power, such UV sources can provide suitable energy levels for sanitization in a specified time. Lower or higher energy levels may also be used depending on the sanitization time constraints.

UV sources such as LEDs can be tailored to provide energy in very narrow bands including, for example, UV-C. Output spectrums can be tailored to provide total spectrums within, for example, ±500 nm, ±100 nm, ±10 nm or ±1 nm or less of the center band frequency of about 250-290 nm or 265-275 nm. This may advantageously affect heating, ozone production, and/or operator safety of the broader spectrum bulbs. LEDs and/or LED arrays in the power range of 1 $mJ/cm^2$ to 400 $mJ/cm^2$, or more, packaged either singly or with multiple source packages to increase total power, provide suitable energy levels for sanitization at high throughput for automated applications. Lower or higher energy levels may also be used depending, for example, on the sanitization time constraints. In various embodiments, one or more UV LED sources may be placed at various locations distributed and directed to illuminate at least one surface to be sanitized. UV LEDs may be distributed in rectangular, linear, curvilinear, circular, spherical, or other patterns to expose one or more regions and/or surfaces to UV radiation. In various applications, predefined LEDs may be selected to operate at selected times to provide a dose of UV radiation. The dose and selection of which LEDs to activate and the timing of their activation may be determined according to the type and/or size of the object (e.g. vial, IV bag, or the like) to be exposed. The LEDs can be activated in series, in parallel, overlapping or the like, and the timing of the activation often depends on the purposes to be achieved, such as high power, long duration with lower power, preserving source lifetime and more. Examples of UV LEDs that may be used in some embodiments are described in, for example, US Published Patent Application 2004/0099869 filed on Oct. 22, 2003, the contents of which are incorporated by reference.

In some embodiments, the UV lamp in the port sanitization system may be cooled and/or cleaned by a flow of clean air. Such air flow may cool and/or substantially reduce particulate or organic solvents from depositing on the lamp surfaces. Connecting it to a low-pressure peripheral duct can force the air to be drawn into the UV lamp housing from just below the fan filter unit outlet (where it is cleanest) and to flow over the UV lamp to provide cooling. In some embodiments, such cooling may be performed without additional air moving elements that may generate air currents that may disrupt controlled laminar air flow patterns in a compounding area.

Example methods to deliver a required dose of ultraviolet radiation to a target may include continuous emission, intermittent emission and pulsed emission. For continuous emission, suitable sources may require warm-up time and typically do not suit repetitive and/or frequent on-off cycles. Examples of such sources include, but are not limited to, mercury vapor lamps, fluorescent backlights, and metal halide lamps, and combinations of these and other sources. For intermittent emission, suitable sources can operate continuously and also have the capability of repetitive and/or frequent on-off cycles (e.g., LEDs, and lasers). For pulsed emission, suitable sources include the sources that are designed to flash at specified frequencies with specified pulse widths, such as flash bulbs using Xenon or other appropriate gases.

In one example of UV sanitization, an optical conduit (e.g., light pipe, optical fiber, optical waveguide) can be used, for example, to reduce transmission losses between at least one UV source and the sanitization target. In some implementations, the optical conduit allows transmission of a particular wavelength range (e.g., a UV wavelength range used for sanitization). The conduit can be placed in close proximity to the UV source such that substantially most or all of the UV light emitted by the UV source (e.g., a diffuse source)

impinges on the entry plane of the conduit. In some implementations, once the UV light enters the conduit, losses within the conduit can be a function of the conduit material and construction. For example, an optical conduit may include one or more optical fibers, or one or more formed structures (e.g., glass or plastic structures). Light exiting the optical conduit may pass through one or more optical lenses. One or more convex and/or concave lenses may be selectively applied (e.g., on a rotating mechanism) to provide selective control of the beam width incident on the surface(s) to be sanitized.

In some implementations, one or more optical conduits can be arranged to gather and/or combine UV light from one or more UV sources and transmit the UV light to one or more sanitization targets concurrently or simultaneously. For example, multiple UV sources can be combined using an optical conduit to focus the UV light onto a single sanitization target. In another example, a single UV source can be split using multiple optical conduits to direct UV light at multiple sanitization targets. In another example, UV light incident on the target surface(s) from a first optical conduit can substantially overlap or combine with UV light emitted from a second optical conduit. In some implementations, one or more UV sources can include a light emitting diode (LED) or a Xenon flash UV source. Examples of flash UV sources are described with reference to FIGS. 26A through 29C of U.S. patent application Ser. No. 11/389,995, entitled "Automated Pharmacy Admixture System," and filed by Eliuk, et al. on Mar. 27, 2006, the entire disclosures of which are herein incorporated by reference.

In some implementations, the optical conduit may include an exit plane arranged in close proximity to the target such that diffusion losses between the conduit exit plane and the sanitization target are substantially minimized. In some implementations, the conduit allows the UV source to be located substantially remotely from a sanitization target (e.g., due to packaging or mounting constraints, and/or to simplify maintenance of the UV source). In some implementations, a remotely located UV source allows maintenance to be performed on the UV source (e.g., replacing a bulb) without contaminating the surfaces to be sanitized (e.g., fluid ports and needles). In some implementations, a remotely located UV source protects users from, for example, a flash from an LED or Xenon flash UV source. In some implementations, the amount of benefit from the conduit can vary depending on factors such as light conduit losses (e.g., coupling or transmission losses), sanitization target size, number of UV sources, conduit geometry, etc. In some implementations, the conduit provides about a 10%, 20%, 30%, 40%, 50%, 60%, 70%, 80%, 90%, 100%, 150%, 200%, 300%, 500%, 1000% or more increase in energy striking the target for UV sources illuminating vial bungs or IV bag fluid ports through a light conduit as compared to the same sanitization target at the same distance from the same UV source without a light conduit.

The PSS as described incorporates one or more systems or methods for holding medical containers (e.g., drug vials, syringes, or IV bags) whose ports are to be sanitized (i.e., receive a sanitizing dose of radiation). Examples of drug vials include, but are not limited to, 1 ml to 100 ml with the associated full range of vial seal/stopper sizes and types. Example bags and/or I.V. containers include, but are not limited to, all sizes of IV fluid bags of solution (e.g., saline solution, dextrose, sterile water and combinations thereof) including, but not limited to, sizes up to 3 liters. In one APAS cell application, the item to be sanitized may be held by the cell robot, or handed off to another holding mechanism. One holder embodiment achieves the holding through the use of a gripper or clip. The gripper or clip in this case may contact the vial on the vial top, neck or body. Another holder embodiment could use a platen on which a vial is placed. Yet another holder embodiment could use a cradle on which the vial is placed. Still another holder embodiment involves the use of vacuum, in combination with the sealing/containment function, to hold vials in place through suction on the top (area to be sanitized). Another embodiment may incorporate a movable platen that is used to firmly engage the vial into the exposure orifice when properly installed by the user, manipulator and/or robot. The movable platen can be driven by a spring, motor, pneumatics or hydraulics. The robot holder/holding mechanism used may be stationary, or may involve moving continuously or in steps through a variety of positions. Additionally, the holding mechanism or method may be combined with another subsystem function to improve cell efficiency. In the case where the object to be manipulated is a vial, the PSS holder may be combined with the vial ID operational function. In the case of IV bags, the PSS holder may be combined with the bag scale/ID station.

In various embodiments, the holding mechanisms/methods may also be generally applicable to syringes. Some options may also apply to the stand alone PSS. For the stand alone PSS system, the operator may hold the item to be sanitized manually in the required position. The holding options described above include embodiments with a stationary holder, or with a mobile holder including 1 or 2 additional axes of motion to position the item for sanitization. In additional embodiments, an automated transfer mechanism may be used to remove the object from the chamber after exposure to the ultraviolet radiation. The automated transfer mechanism may include a robotic manipulator and/or a rotating platen and may manipulate or move the object in response to a sequence of commands automatically generated by a processor executing a program of instructions. Location features may be included to aid in the positioning of the object by an operator (e.g., pharmacy staff) in the correct location in the PSS chamber.

Figure 3A:
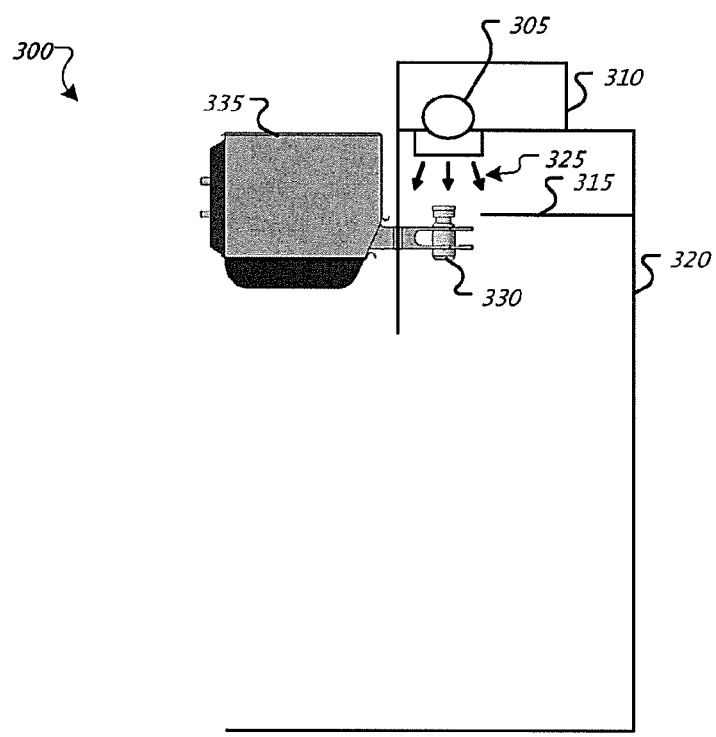
FIGS. 3A-3C show cross-sectional views of an illustrative port sanitization system (PSS).
Figure 3B:
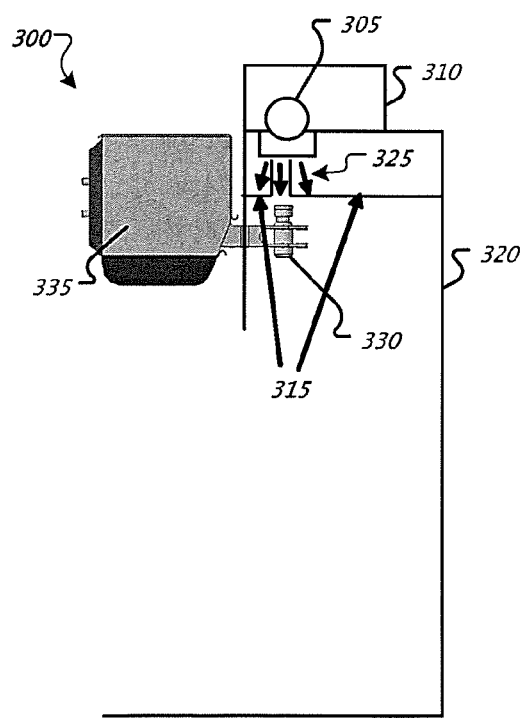
Figure 3C:
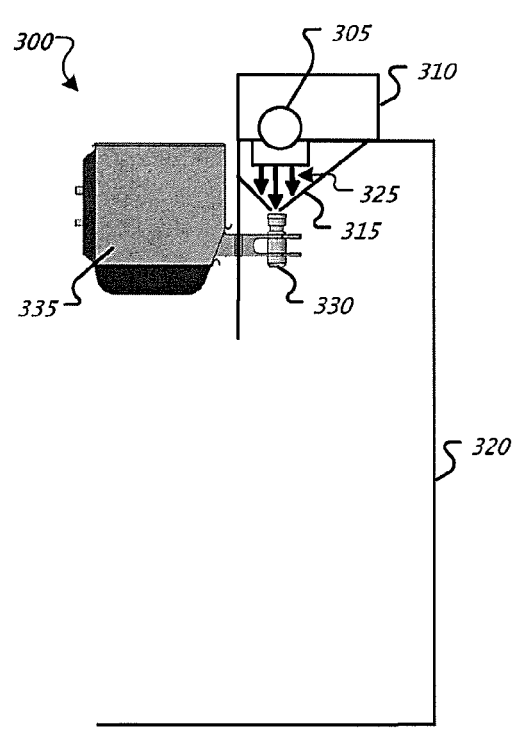

FIGS. 3A-3C show cross-sectional views of an illustrative PSS 300. In an illustrative embodiment, a PSS 300 may be used to sanitize items within an automated pharmacy compounding device, such as an APAS cell 100, an example of which was described with reference to FIGS. 1 and 2. In this example, the PSS 300 can be used to sanitize items that include, but are not limited to, drug vial ports, IV bag ports, and syringes. The sanitizing process performed by the PSS 300 may be used alone or in combination with one or more other cleaning processes, such as an alcohol wipe.

The PSS 300 may be used to perform operations to sanitize objects placed within a PSS chamber. In this example, the PSS 300 includes an ultraviolet (UV) lamp 305, a lamp housing 310, a baffle 315, and a chamber wall 320. The chamber wall 320 may substantially reflect and/or absorb radiation so as to substantially contain UV radiation 325 from the UV lamp 305 within the PSS chamber. The UV radiation 325 from the UV lamp 305 may illuminate an object 330 placed within the PSS chamber. In this example, the object 330 is a drug vial that is positioned to be exposed to the UV radiation 325 by a manipulator 335. The manipulator 335 may be a robotic gripper.

FIGS. 3A-3C show a single chamber embodiment where the lamp housing 310 and the UV lamp 305 are mounted above the object 330 with the UV radiation 325 directed downward. In other embodiments, one or more UV radiation sources may be directed upward and/or from the sides, either alone or in combination with the downward directed UV lamp 305. An illustrative UV radiation source for the lamp 305 is a Xenon lamp. The size of the light aperture in the baffles 315 may be suitable for the objects being sanitized. The object 330 may be presented to the UV radiation source by mechanical or robotic mechanisms.

The PSS 300 of FIG. 3A includes a baffle 315 arranged to form an opening to pass the light onto an object 330. The PSS 300 of FIG. 3B includes baffles 315 arranged to provide a substantially cylindrical or tubular, vertically oriented lumen through which to illuminate an object 330. The baffles 315 may have reflective surfaces. The PSS 300 of FIG. 3C includes baffles 315 arranged to form a partial conical surface with an aperture to direct substantially all light to an object 330 disposed near the aperture. Other similar arrangements of baffle configurations may be used to direct a substantial fraction of the light that enters the PSS chamber to an object placed near one or more apertures like those of FIGS. 3A-3C. In some embodiments, the baffling may be automatically or manually reconfigurable to provide suitable illumination of the object. For example, the baffles may be on a rotatable carousel that can be repositioned (e.g., by an actuator motor), to position the most effective baffle to illuminate the size, type, and/or shape of the object.

The PSS 300 may be adapted for integration into an APAS cell 100, or configured for stand-alone (e.g. table-top, free-standing) operation for use in a hospital pharmacy or similar environment. Information to identify a medical container (e.g., content, shape and/or size) may be received by a controller from a pharmaceutical prescription database. In the hospital pharmacy type of environment, pharmacy staff may prepare prescriptions by using an extension tool (e.g., tongs) to grasp the object to be sanitized and place it into the PSS chamber for sanitization. Location features (not shown) may be included to aid in the positioning of the object by the pharmacy staff in the correct location in the PSS chamber.

FIGS. 4A-4C show cross-sectional views of an illustrative PSS 400 that accepts variously sized objects to be sanitized. In FIG. 4A, an object 405 is a large vial, in FIG. 4B, an object 405 is a small vial, and in FIG. 4C, an object 405 is an IV bag. In each example, a manipulator 410 may move along a trajectory suitable for positioning an object in a suitable location to be sanitized in the PSS chamber 400. In FIG. 4C, the IV bag 405, for example, may be flexed (e.g., if empty) to be positioned in the PSS chamber 400 so that an IV bag port 415 can be sanitized before making physical contact with a syringe (e.g., to perform a manual or automated fluid transfer operation).

Accordingly, the object to be sanitized need not provide a primary light seal. Chamber walls 420, in combination with the manipulator 410, may provide effective light containment. The chamber walls 420 may include features such as baffles 425, reflective surfaces, and/or absorptive surfaces to further minimize escape of UV radiation from the PSS chamber 400.

Figure 5:
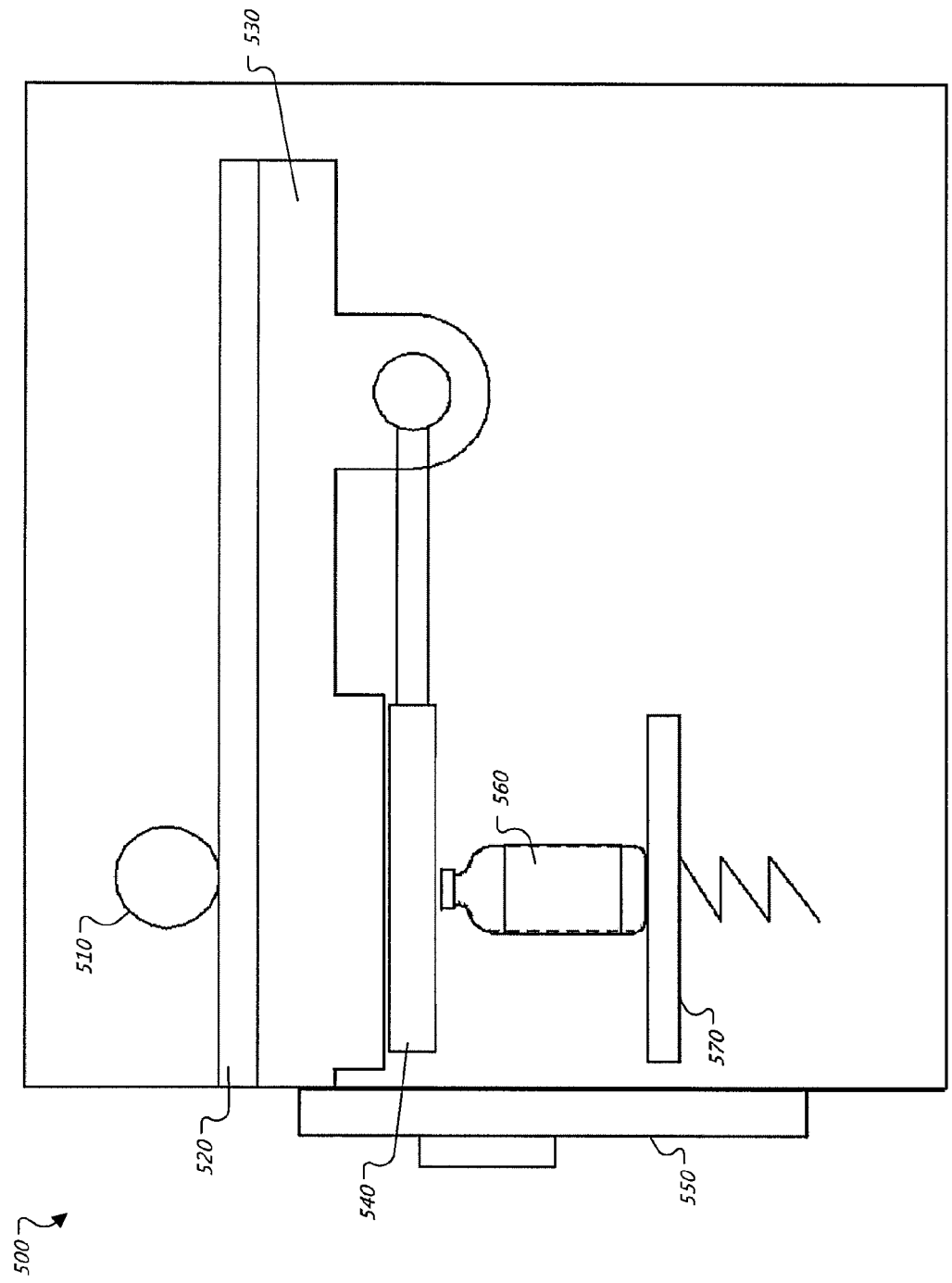
FIG. 5 shows an illustrative enclosed PSS.

In one example of the PSS, walls may substantially enclose the chamber, with at least one wall having an opening for receiving a medical container and a portion of the transfer mechanism. FIG. 5 illustrates one exemplary embodiment of an enclosed PSS 500. A vial 560 to be sanitized can be placed on a spring loaded platen 570 by either a robotic or manual method for the case of a stand alone system. A seal assembly 540 is pushed up by the spring platen 570 through the vial 560 to form a seal with a pressure chamber 530. The pressure chamber 530 can substantially form a pressure seal between the vial port and the seal assembly by reducing the pressure of the chamber to provide a substantial vacuum. In some examples, the pressure chamber 530 is evacuated to promote a light tight seal. In various embodiments the pressure chamber may operate as an interlock that disables radiation output unless a measurement signals from a pressure sensor in the chamber confirms that pressure in the chamber meets predetermined criteria (e.g., maintains at least a minimum threshold vacuum or positive applied pressure level), thus confirming that the vial port is properly seated in the seal assembly 540 and that the seal assembly 540 is properly seated against the pressure chamber 530. The depicted example shows a hinged seal assembly. Other variations may include a rotating carousel of seal assemblies or simply a single fixed seal assembly. The pressure chamber 530 may be at least partially enclosed on the top by UV transparent glass 520 or equivalent. The pressure/vacuum may be monitored in the chamber 530 to determine when to enable the UV source 510. Other criteria may be used to enable the UV source such as a signal indicating a door 550 is closed to substantially contain radiation within the PSS 500.

Figure 6:
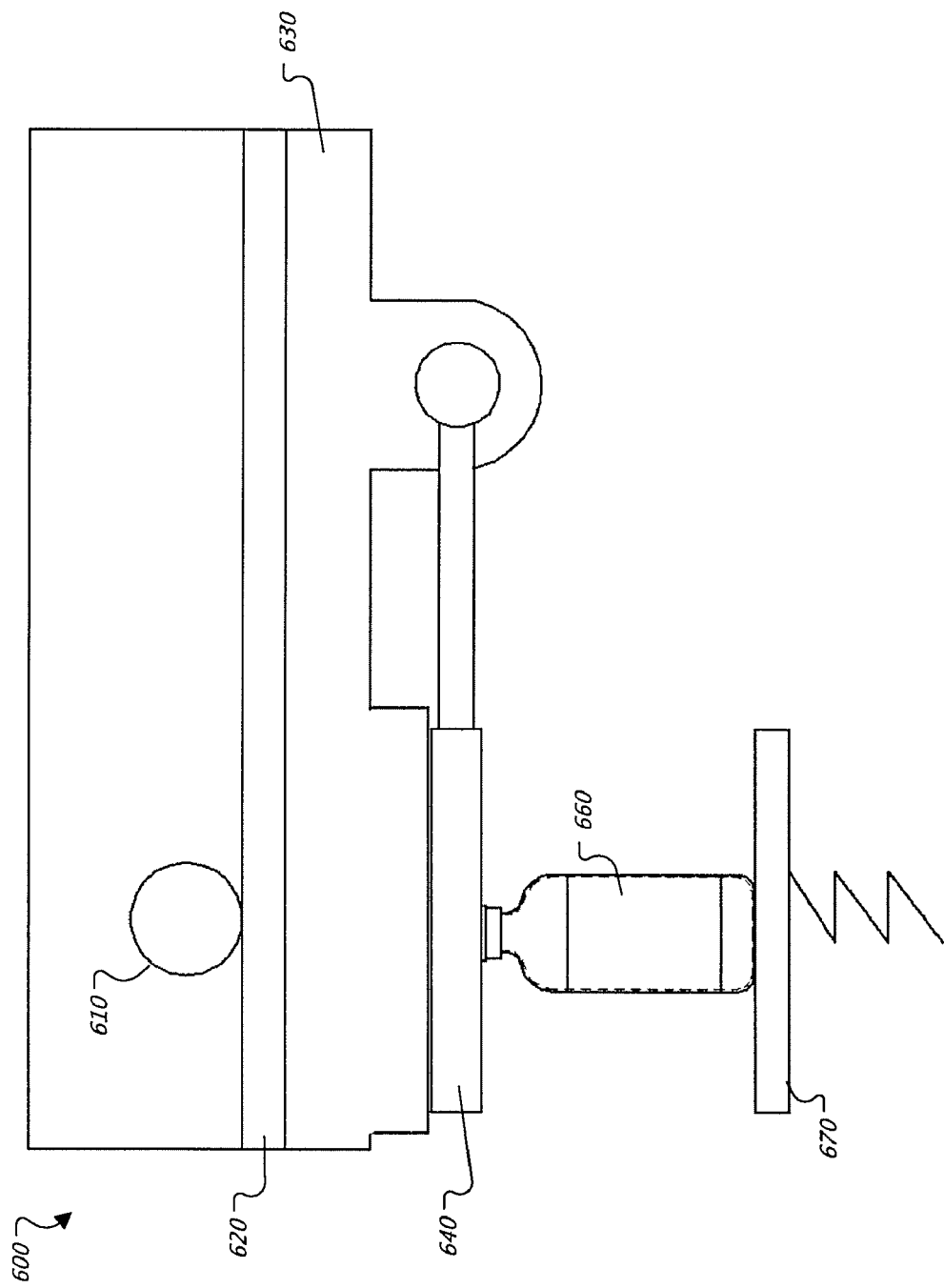
FIG. 6 shows an exemplary PSS without surrounding walls.

FIG. 6 illustrates an exemplary PSS 600 without walls surrounding the item to be sanitized 660. The seal assembly 640 is shown as a hinged seal assembly; other embodiments may include a rotating carousel of different seal assemblies or a single fixed seal assembly. Spring loaded platen 670 can be used to push the vial 660 and seal assembly 640 upward to seat with the pressure chamber 630. Alternatively, spring loaded platen 670 can be omitted and the manipulator or operator can hold the vial 660 in the position to seat the seal assembly 640. In some other embodiments, at least one seal assembly is operable to provide an adjustable aperture (e.g., iris) or masking profile for controlling the size, shape, and/or location of the predetermined region to be exposed to the dose of radiation. If vacuum is used in the pressure chamber 630, the manipulator or operator may release its grip of the vial 660 and rely on the vacuum to hold the vial 660 in place while sanitization process takes place. When vacuum is generated indicating a proper seal, the UV source 610 is enabled and the dose is delivered though the UV transparent glass 620 to the port of the vial 660.

Figure 7:
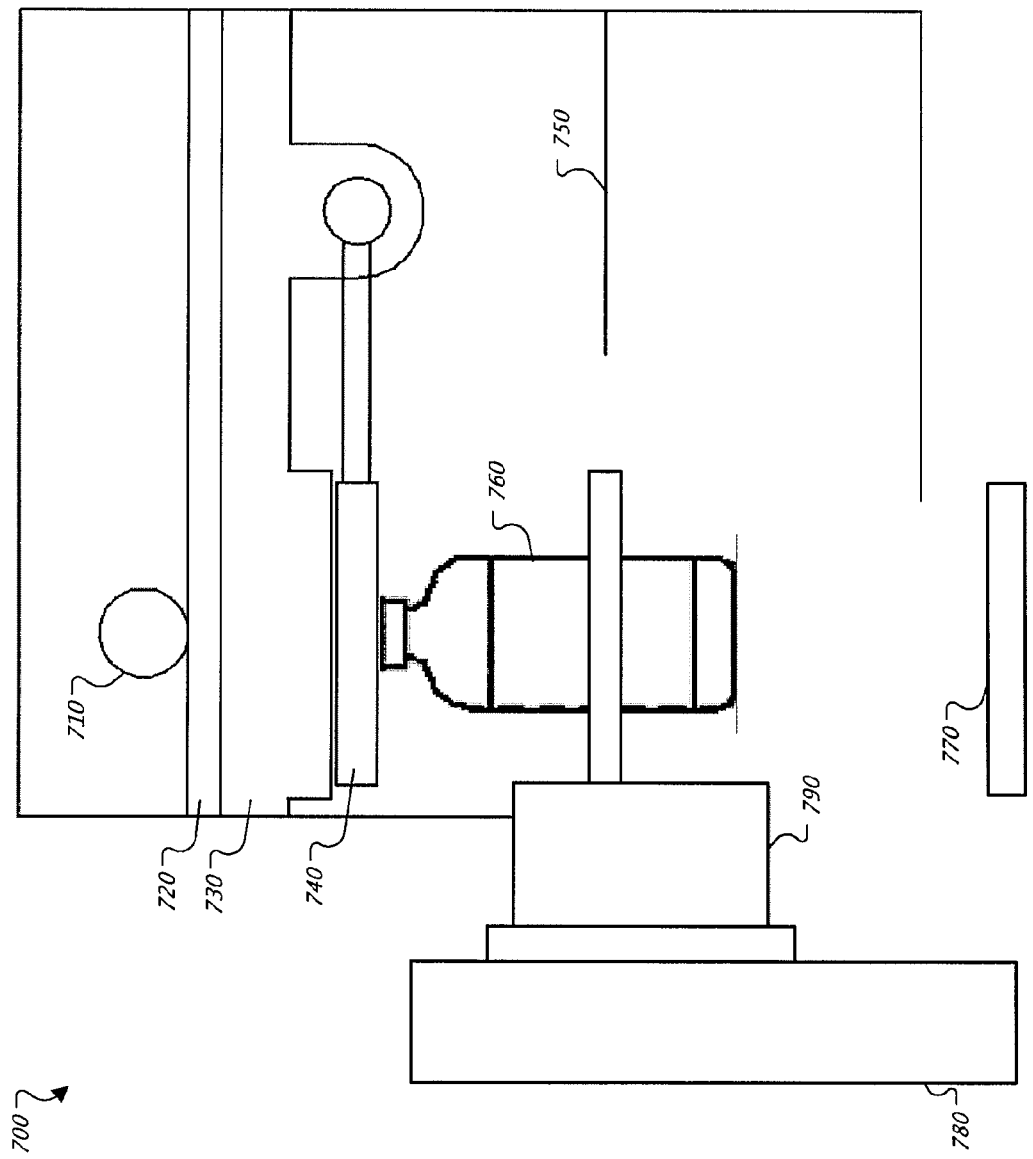
FIG. 7 shows an illustrative PSS with gripper mechanism.

FIG. 7 shows an exemplary PSS 700 that includes a gripper and an axis of motion. In this example the operator (in the manual case) or robot places the vial 760 onto the platen 770. The gripper 790 is lowered by the motorized slide 780 and the vial 760 is picked up by the grip fingers 795. The vial 760 is then elevated to the seal assembly 740 which is seated against the pressure chamber 730. A secondary light barrier such as a baffle 750 may be used. When pressure/vacuum is generated indicating a proper seal, the UV source 710 is enabled and the dose is delivered though the UV transparent glass 720 to the port of the vial 760.

Depending on the safety environment, containment of the UV energy may not be needed. For example, some products (e.g., sterile water bags) may not be affected by UV light exposure. If personnel safety in terms of sufficient UV containment is provided by, for example, the cell walls and doors, sanitization in an enclosed setting may not be required. Where operational circumstances permit reduced light containment specifications, processing and/or transport times may be reduced by simplified motion trajectories, thereby enhancing throughput for manual or automated sanitization processes. In some embodiments, one or more optical sensors may be located in and around the PSS to detect the presence and/or intensity of "leaked" radiation that may escape from around the light seal, through the medical container, or otherwise, from the primary optical path between the radiation source and the predetermined target region. A controller may monitor such sensors, and take some corrective action should the detected leakage exceed a predetermined level. Examples of corrective actions may include, but are not limited to, generating a notification signal (e.g., electronic message to an operator, warning light, or the like), disabling the radiation source, or attempting to reconfigure the light seal assembly by, for example, selecting a different light seal that may provide improved sealable engagement with the current medical container. In this way, the optimal available light seal for any (perhaps unrecognized) medical container may be determined and recorded in a data store for use in future operations based on leakage sensor feedback.

Figure 8A:
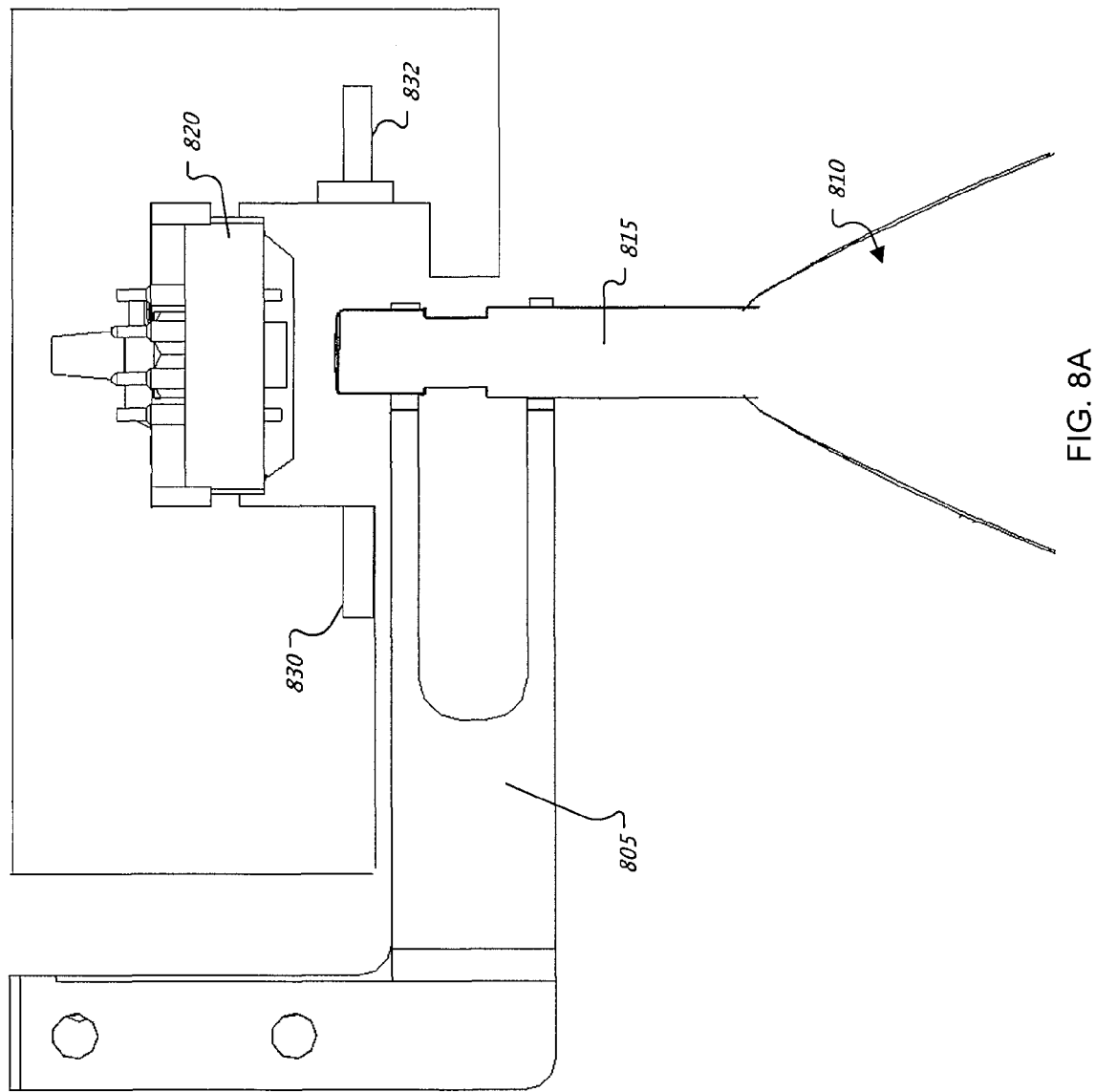

FIGS. 8A and 8B illustrates an exemplary IV bag and drug vial sanitization, respectively. In FIG. 8A, a robot (not shown) grabs an IV bag 810 from a prior station (e.g., an IV bag scale or rack) using robot fingers 805 and transports the bag 810 to a PSS. The robot then places the bag port 815 into close proximity with a UV source 820. A light or laser emitter 830 and detector 832 are used to detect the presence or absence of a bag port. The emitter 830 emits a light or laser beam that can be detected by the detector 832. When a bag port is placed between the emitter 830 and detector 832, the beam is broken which then sends a signal to the controller (not shown) to enable the UV source 820. When the robot places the bag port 815 in the correct position, the port 815 breaks the emitted beam, thereby enabling the UV source 820 to illuminate the portion of the port to be sanitized. After the required dose is provided, the robot moves the bag 810 to the next station, which could be any a scale, a temporary holding station, or a syringe manipulator.

A shield/mask may be used to prevent UV from hitting the bag contents or escaping into the cell. For bags, UV exposure may not be an issue unless there are drugs in the bags. The escape of UV into the surrounding chamber or environment may be controlled by small clearances and/or the shape of the robot fingers 805 that can cover most of the opening. Surfaces of the robot or actuator that may be exposed to UV radiation may be treated to promote controlled reflection, absorption, diffusion, or a combination of these or other In one implementation, a flexible mask with a slit is used. The robot pushes the bag port through the slit so that the mask sits between the upper and lower protrusions of the robot fingers 805. This effectively seals the entire lower portion of the light path, while leaving open the path between the robot fingers and the assembly surface just above it (where the emitter 830 sits).

In FIG. 8B, an appropriate movable aperture seal assembly 840 is moved into alignment, based on the identifying information about the drug vial to be sanitized 812. The movable seal assembly 840 has some vertical compliance and rests just below two mating surfaces 850 when aligned. The two mating surfaces 850 may be two machined surfaces. A robot (not shown) grabs the vial 812 from a prior station (e.g., vial weighing station or rack, container cover/seal removal station, or the like) using robot fingers 805 and takes the vial 812 directly underneath the seal assembly 840. The robot then moves the vial 812 upward, deforming a flexible mask 860 and bringing the movable seal assembly 840 into contact with the mating surfaces 850. A vacuum port (not shown) is used to draw air from the chamber created as a result of the seal assembly 840 contacting the mating surfaces 850. A pressure sensor (not shown) is used to measure the pressure inside the chamber. If the pressure decreases to a defined level, the vial 812 is in the correct position and a substantial light seal has been created. An o-ring or other gasket type material may be used with the mating surfaces to improve light seal. A UV source 820 is then enabled, thereby illuminating the portion of the vial port 817 to be sanitized. After the required dose is provided, the robot moves the vial 812 to the next station, which could be a scale, a temporary holding station, or a syringe manipulator. In one implementation, light seal may be provided by placing a cover over the drug vial to be sanitized.

Some embodiments of the PSS chamber may be customized for the specific range of objects to be sanitized, taking into consideration requirements such as: object access requirements to the light source, object size, light containment, and distance of the object from the light source.

Figure 9A:
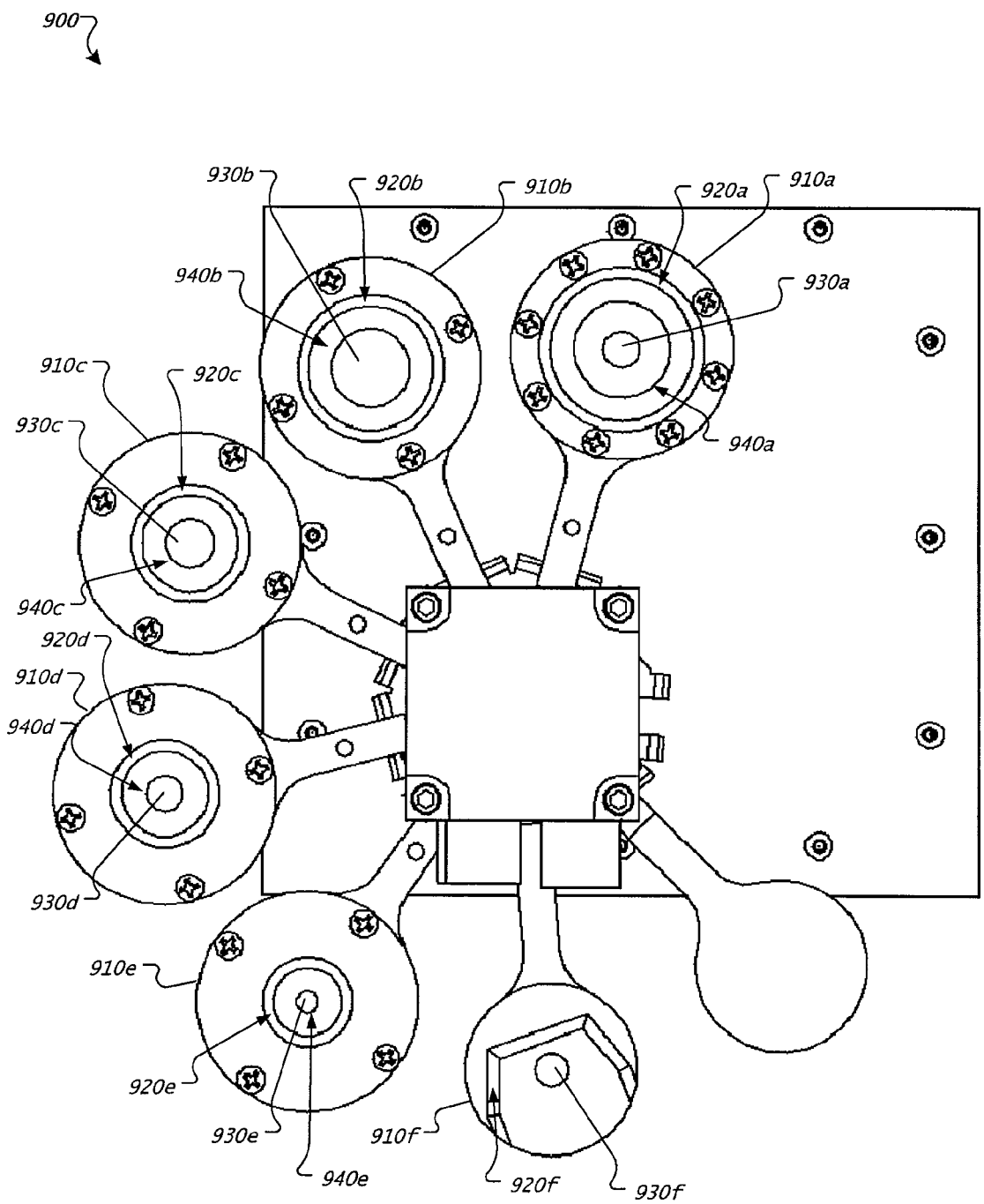
FIGS. 9A and 9B show a top view and an isoparametric view of an exemplary cleaner carousel, respectively.
Figure 9B:
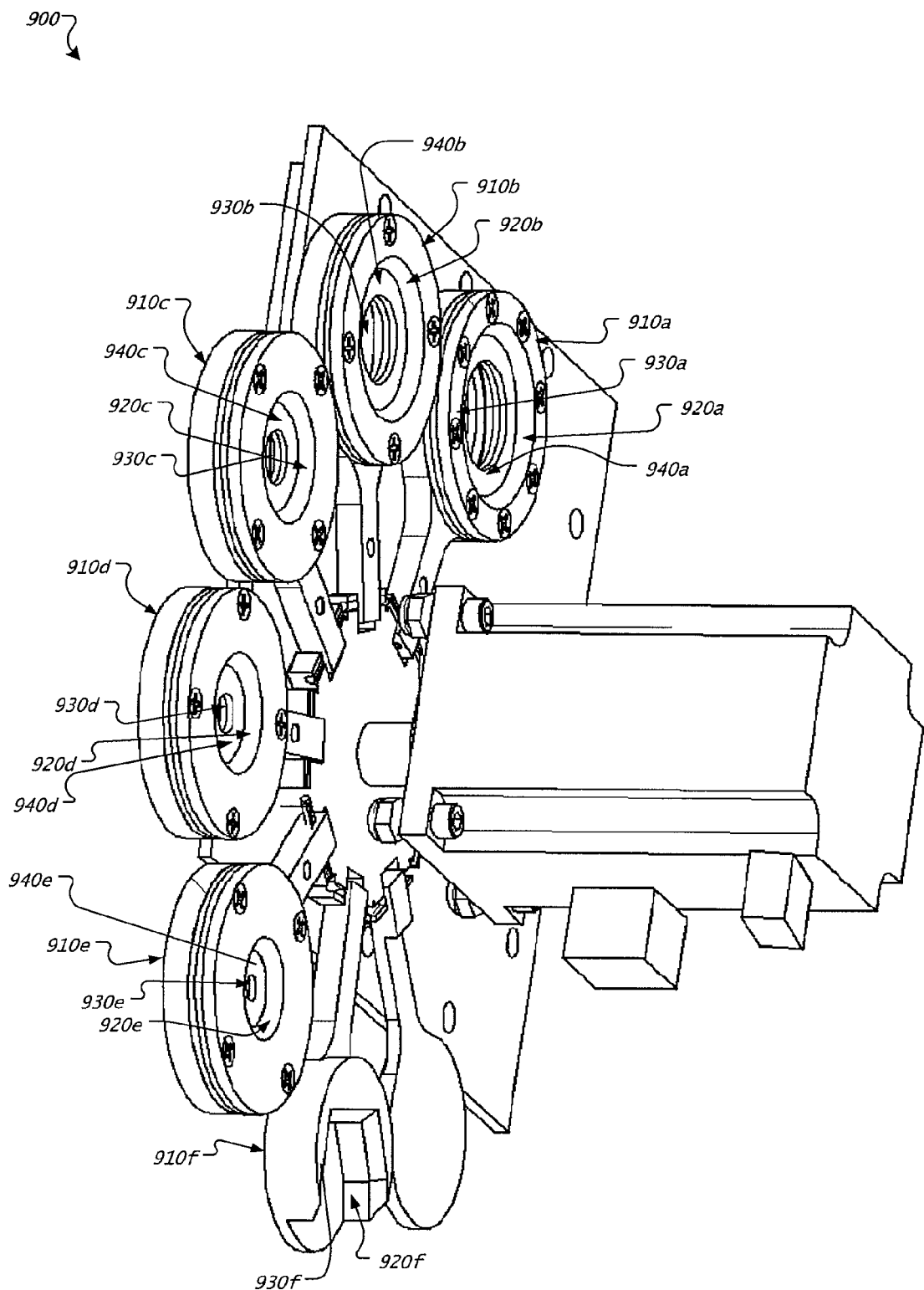

In various embodiments, the sealing systems or methods may be designed not to touch the areas of the stopper or fluid transfer port to be sanitized. This may help to protect the areas to be sanitized from both microbial and drug cross-contamination. Referring to FIGS. 9A and 9B, aperture seal assemblies 910a-f are designed to incorporate chamfered guides 920a-f to aid engagement. To engage an item to be sanitized (e.g., a vial), the operator (in the manual case) or robot centers the item in the aperture 930. If the item position on insertion is too far out, it will not engage. The size of the aperture 930 is configured to be larger than the size of the areas to be sanitized, so if engaged the areas to be sanitized will not be touched and full exposure of the areas to be sanitized will be assured. Proper engagement provides sealing between the pressure chamber (not shown) and the seal assembly 910. The seal assemblies 910a-f can be removed and/or interchanged from the rotating or fixed carousel 900.

In some embodiments, a rigid, semi-rigid, or flexible gasket 940 (e.g., rubber, foam, plastic, or flexible UV blocking or reflective material) may be formed around an aperture 930. When a fluid port of a vial or IV bag is to be sanitized, an operator in a pharmacy or a robot arm in an APAS cell may place the fluid port to be sanitized in proximity to the aperture 930 such that the gasket 940 forms a substantial light seal interface with a body of the vial or IV bag. The aperture 930 may provide a substantially UV-transparent window through which one or more surfaces on the fluid port may be exposed to ultraviolet radiation through the window.

The aperture gaskets 940a-f, may generally include, but are not limited to, materials that are compliant to form a seal (e.g., silicone rubbers). Such materials may also be selected and screened to provide suitable resistance to heat and UV exposure for the applicable embodiments of the PSS. One embodiment comprises several gasket apertures 930a-f (see FIGS. 9A and 9B) that combine to cover a wide range of vial seal/stopper diameters. Each aperture 930 may handle a sub range of vial top sizes. Sealing is achieved on the outer edge of the metal part of the vial top, removed from the stopper or port puncture area in the center. These apertures 930a-f may be in fixed locations, or indexed via a variety of means to a fixed interface location. Guiding features may also be incorporated to guide the travel of the item to be sanitized into the exposure aperture. The quality of the seal is verified prior to and during exposure by monitoring the pressure/vacuum in the pressure chamber (not shown).

Instead of, or in combination with, a flexible boot, some embodiments may provide a receptacle 910f to receive a fluid port in proximity of the UV exposure port. The receptacle 910f may be sized to receive one or more sizes and styles of fluid ports for IV bags, and one or more sizes and styles of fluid ports for vials. A concave opening receptacle 910f may be adapted to receive a range of sizes. One or more differently sized and/or shaped receptacles may be provided. In some embodiments, receptacles may be interchanged to accommodate a wide range of items to be sanitized. Different receptacles may have locating pins, rotating and/or sliding features to retain a receptacle being used. Interlock features may be integrated into each receptacle. For example, proximity or pressure sensors may be used to determine when a receptacle is properly installed and a properly sized vial or IV bag fluid port is being inserted or pressed into the receptacle to be exposed to the ultraviolet radiation.

In some embodiments, the automated transfer mechanism may provide at least a partial light seal around at least a portion of the opening on the PSS chamber wall. For example, a manipulator may be adapted to provide a thin (e.g., pencil-like) extension apparatus to extend the reach of the manipulator through a reduced width (e.g., narrower) slot in the narrow portion of the opening in the PSS chamber housing. Such extension apparatus, or the external portion of the manipulator itself, may be provided with baffling to provide either an internal or an external light seal around some or all of the openings in the PSS chamber housing. For example, a flexible rectangular baffling (e.g., plastic, rubber, or foam with reflective or absorptive coating) may be used to provide a substantial UV light seal over some or all of the narrow and/or wide openings in the PSS chamber housing when an object is positioned to receive UV radiation.

In some embodiments, the object to be sanitized may provide an effective light seal. The design of the baffles shown in FIGS. 3B-3C may be such that the object effectively seals the opening in the baffle when the object is brought into substantial contact with the baffle. Also, the baffle design may be compliant (e.g. flexible baffle material, spring mounted baffle assembly, or bellows) such that some tolerance in the positioning of the object against the baffle is afforded. The opening in the baffle may be sized to maximize the amount of UV radiation on the targeted area to be sanitized.

In some embodiments, cooling and venting systems may be included to, for example, cool the UV source, cool the sealing materials and their mounting structures, cool the object(s) to be sanitized, and/or to remove ozone gas that may be generated by some UV sources.

A typical implementation for cooling and venting may utilize the suction piped from the APAS exhaust fan plenum to draw cooling air through the PSS as required, and at the same time could be used to vent ozone if the applicable APAS cell has a vented exhaust. Another embodiment may utilize local fans to provide cooling air, drawing air from the clean cell air to provide cooling. This air could flow back into the cell or be routed to the local exhaust air duct. In still another embodiment, both exhaust suction and local fans may be combined to provide increased air flow, and/or to capture ozone. In yet another embodiment, cooling air can be obtained directly from HEPA filtered fan filter units. In one implementation, a combination of conductive and convective heat transfer mechanisms are used to manage the thermal load of the UV source. For any of these implementations, an ozone catalyst may be placed in the air flow to reduce the amount of ozone that is generated and re-circulated. The catalyst, in one example, may be local to the PSS housing to reduce its size and immediately reduce ozone levels. The catalyst may also be placed in line with the exhaust filter to scrub ozone repeatedly and/or when the cell operates in a recirculation mode. In some embodiments, the input air may be filtered to prevent particles from getting to the object(s) to be sanitized. The filtered air may also prevent particles from contacting the UV lamp, thereby increasing bulb life and efficiency. In some cases, the PSS may be designed for application within the APAS cell ISO class 5 clean air environment.

Figure 10:
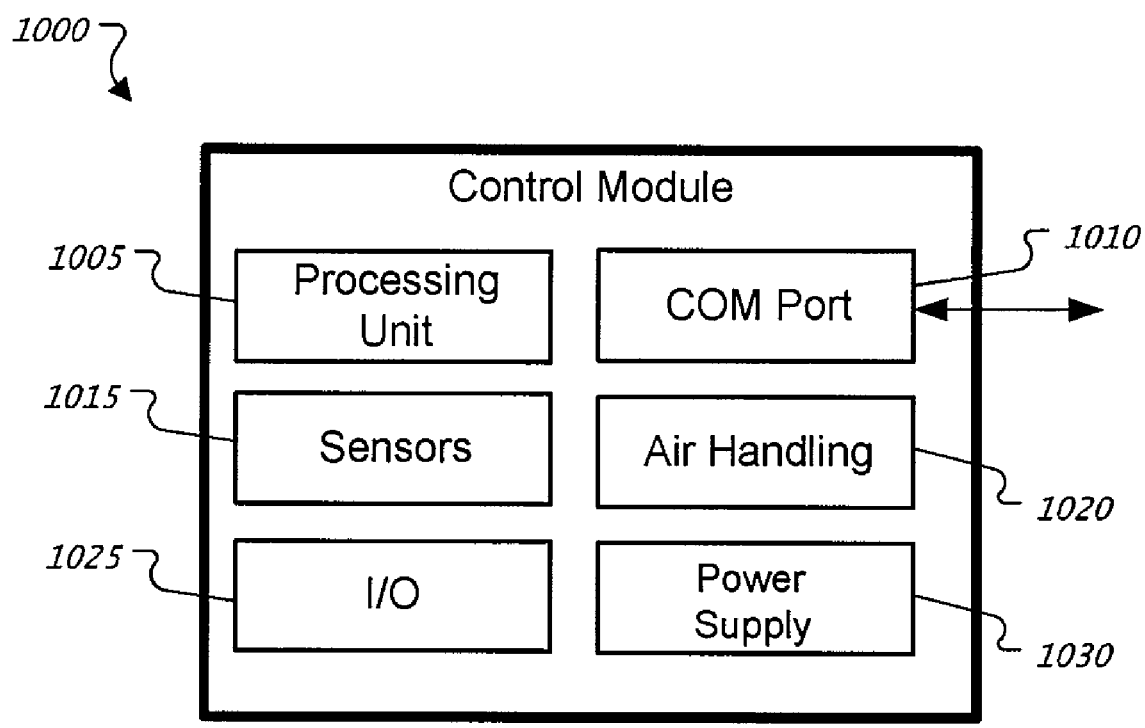
FIG. 10 is a block diagram of an exemplary control module for the PSS of FIGS. 3A-3C.
Figure 11A:
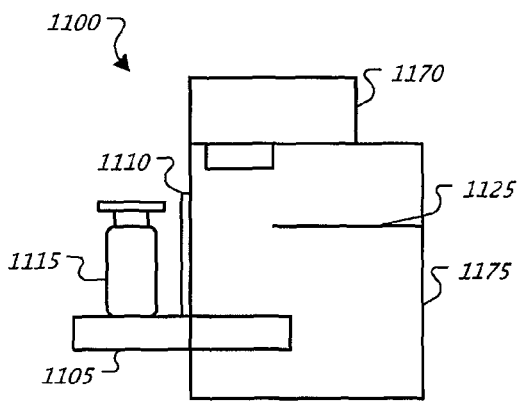
FIGS. 11A-11F show cross-sectional views of an illustrative PSS in an APAS cell.
Figure 11B:
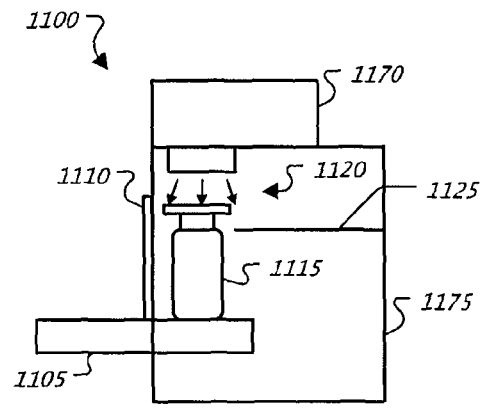
Figure 11C:
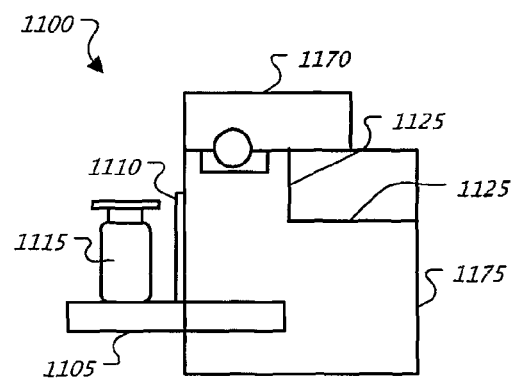
Figure 11D:
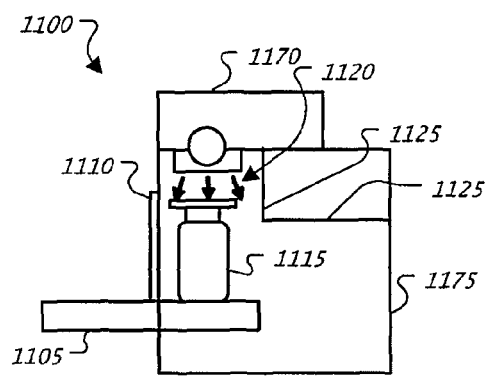
Figure 11E:
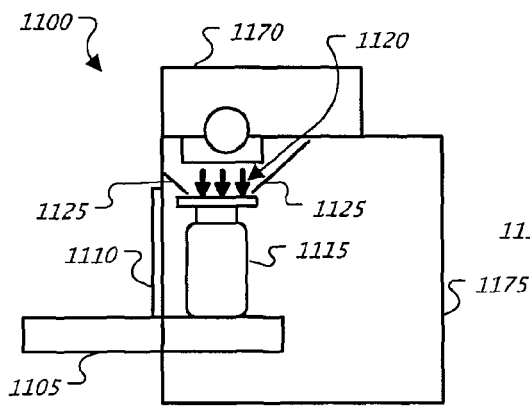
Figure 11F:
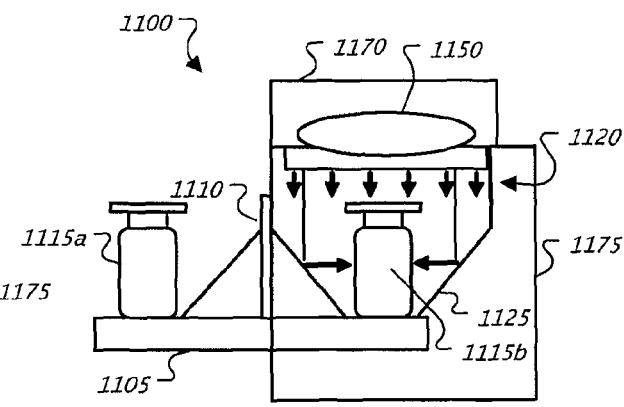

FIG. 10 is a block diagram of a control module 1000 for the illustrative PSS 300 of FIGS. 3A-3C. In an illustrative embodiment, the PSS 300 discussed herein may include a PSS chamber, a UV lamp assembly, and the control module 1000. The control module 1000 may include a processing unit 1005, a COM port 1010, one or more sensors 1015, an apparatus for operating an air handling system 1020, an input/output (I/O) port 1025, and a power supply 1030. The processing unit 1005 can be used to supervise, monitor, and control operations according to programmed instructions and/or hardware configurations (e.g., analog, digital, PAL, and/or ASIC circuits). The sensors 1015 may include, but are not limited to, temperature, smoke, contaminant, vibration, position, and light intensity sensors. The I/O port 1025 can be used to receive and send signals to the sensors 1015 and/or actuators (e.g., motors, UV lamp) in the PSS 300. In some embodiments, the control module 1000 may send and/or receive status and control information to or from a host computer or controller via the COM port 1010. The COM port 1010 may be serial or parallel, and may use packet or non-packet based communication protocols (e.g., RS-232, USB, Firewire) to receive and/or send signals to a master controller. An example of the apparatus for operating an air handling system 1020 was described with respect to FIG. 22 of U.S. patent application Ser. No. 11/389,995, entitled "Automated Pharmacy Admixture System," and filed by Eliuk, et al. on Mar. 27, 2006, the entire disclosures of which are herein incorporated by reference. The elements in the control module 1000 can combine to operate the PSS 300 to sanitize objects in pharmaceutical applications. In some embodiments a user interface 1035 may be included. A stand alone device would be one example where a user interface 1035 would be included.

A PSS may use system information available to an APAS controller, for example, to optimize the UV sanitizing process. For example, the APAS cell 100 may contain the control module 1000, as shown in reference to FIG. 10, to control its operations that may transfer control information (e.g., indicative of the next object to be sanitized) to the PSS 300 via the COM port 1010. Such control information may include optimal waveform, amplitude, pulse repetition number and rate, object size, type, and/or shape-related information. The controller in the PSS 300 may respond by configuring the power supply 1030 and trigger controls to generate a sanitizing profile tailored to sanitize the next object. Such optimization promotes effective sanitizing without generating unnecessary heat, consuming unnecessary energy, prematurely aging the flash element, or introducing unnecessary delay in the sanitizing process. In some embodiments, the robotic arm may be unable to perform other tasks during the UV sanitizing process. In other embodiments, the robotic arm may release the object, perform one or more other actions, and return to grasp and convey the object after sanitization is complete.

In response to a start signal, a dose of ultraviolet radiation may be delivered. The dose may be according to a pre-programmed set of instructions, at a specified intensity, duty cycle, repetition rate (e.g., fixed or variable), and number of pulses, or total energy. The start signal may be generated by a switch that is pressed when the body of the object is pressed into the boot, or a proximity sensor (e.g., optical sensor, Hall effect sensor to detect robot arm, or the like) detects the fluid port in position or other relevant features, a signal generated by a controller or another switch (which may be manually pressed), or a combination of such these or other detection techniques.

In some implementations, a UV light sensor may be provided to measure the UV light intensity to monitor the sufficiency of a light pulse. Sensors may be used to monitor the condition of the bulb(s) and the intensity of the emission and/or flash. This monitoring may take place during normal usage and/or as part of a regular maintenance schedule. The sensors may also be monitored to confirm that the appropriate light dose has been delivered. If, for example, the processing unit determines that a UV waveform fails to meet an average minimum threshold over multiple pulses, then the processing unit may generate a fault signal over the COM port 1010. In some embodiments, a sensor may measure the approximate total energy delivered, and send feedback information to a controller. The controller may enable UV output until a predetermined threshold of energy is delivered. Additionally the sensors could be used as part of a regular (e.g., daily) self-diagnostic routine that would warn operators of diminished emission from the UV source, thus allowing for replacement of said source prior to failure. In some embodiments, a fraction of the UV energy is tapped using mirrors or other reflective, or partly reflective, media. This allows the use of sensors having lower energy handling capacity to monitor the total output from a UV source.

In some embodiments, a sensor (e.g., light beam, proximity, contact, or vacuum/pressure) may be included in the PSS chamber to monitor the position or proximity of the object to be subjected to the UV radiation. The sensor may also be used to monitor the position or proximity of an item displaced by the presence of the object (e.g. switch) with respect to the bulb. The sensor may provide an interlock such that the bulb power cannot be enabled if the object is not in the correct position. Sensors may also be used to monitor airflow and shut down the system if inadequate airflow is detected. The bulb or array of bulbs/lamps/LEDs may have temperature and air flow monitoring.

In various examples, interlocks may advantageously provide enhanced operator safety in APAS cells and stand alone embodiments of the PSS, proper and reliable operation of the PSS, and/or protection of PSS equipment from damage or misuse. For example, an interlock may be provided to disable the light source until a portion of the object is in the PSS chamber such that a substantially complete light seal is formed to prevent substantial light from escaping. Suitable interlocks may include, but are not limited to, temperature monitoring of light source(s), door(s) on the PSS or the APAS cell or both, light leakage sensing, vacuum seals, air flow, position sensors, ozone level monitoring, and laser.

For manual operation, some embodiments may include a feedback signal to indicate to an operator that the UV profile has completed, or that the item to be sanitized has been exposed to the selected dose of UV. In some embodiments, a display may indicate an exposure level, such as based on time, number of pulses delivered, or total energy delivered. In some embodiments, the operator may control the exposure level based on how long the item is pressed into the boot.

In an exemplary embodiment, the PSS operates as follows. An automated transfer mechanism, such as a robotic arm, retrieves a medical container (e.g., drug vial or IV bag) from an inventory. From the multiple radiation seal assemblies that cover medical containers with different sizes and shapes, the controller of the PSS system determines which radiation seal assembly corresponds to the medical container retrieved, based on the size and/or shape or the like of the medical container. The robot arm can then present the medical container to the ultraviolet light source of the PSS by engaging the medical container with the corresponding radiation seal assembly. Or the robot arm can place the medical container on a holding apparatus, which can then be actuated to couple the medical container with the corresponding radiation assembly proximate the UV source. The controller then instructs the UV light source to emit UV light at the correct intensity and for the needed duration to achieve the desired effect of sanitization of the exposed fluid transfer port (e.g., drug vial seal/stopper or port or IV bag injection port) either in a pulsed or continuous wave form. If the item being sanitized cannot be exposed to the emitted spectrum (for example, UV light can affect the drug contained in a vial), the sealing/containment system or method may ensure that the drug or IV fluid container and/or contents is exposed to substantially reduced or no UV light as required. If the item being sanitized is not affected by exposure to UV light, the sealing/containment system or method may be designed to only limit exposure to the operator, or not be included at all if the potential outcome of exposure is acceptable. The cooling, purging and or venting system keeps the PSS and item being sanitized cool and vents or otherwise controls the buildup of ozone gas if any. The control system controls all aspects of the PSS operation. Monitoring on the system confirms that the correct UV exposure was produced, and that the target was in the correct location to receive the dose. Interlocks and safety mechanisms ensure that the UV source will not operate without appropriate safeguards or conditions in place. After the PSS sanitizes selected surfaces (e.g., drug vial ports and IV bag ports) using an ultraviolet (UV) light, a fluid transfer operation may be performed via the sanitized fluid transfer port.

Some embodiments may provide one or more further features. For example, in cooperation with the features such as interlocks, sensors etc. the sanitization process may be initiated by user input (e.g., by the touch of a button or other trigger device). There may be audible and or visual indications to cue the operator or inform of progress. The operator may have settings available for such things as exposure time, size of port, and height of vial for example.

FIGS. 11A-11F show cross-sectional views of an illustrative PSS 1100 in the APAS cell 100 of FIG. 1. The PS 1100 can use a rotating platen 1105 with a perpendicular vertical wall 1110 to position an object 1115 to be sanitized. Except for differences as noted or where not applicable, the discussion above regarding embodiments of the PSS 300 are generally applicable to embodiments of the PSS 1100. For example, the PSS 300 may operate using a control module, an example of which is described above with reference to FIG. 10.

The object 1115 to be sanitized is loaded on the platen 1105 external to the PSS chamber. The platen 1105 is rotated using an appropriate drive mechanism, (e.g., stepper motor, servo motor, mechanical linkage coupled to a solenoid) to position the object 1115 inside the PSS chamber where it can be exposed to the UV radiation 1120. The vertical wall 1110 serves as a baffle to substantially provide a light seal for the chamber that may keep most of the UV radiation 1120 from escaping. In some embodiments, sensors (e.g., encoder on platen shaft, index mark using Hall effect sensor, opto-interrupter, etc.) may be used to detect when the platen 1105 is in position for loading or pulsing, or when the walls 1110 are in a sealing position. While positioned in the chamber, the object 1115 may receive a dose of UV radiation, as has been described. The platen 1105 then rotates to position the object 1115 (portions of which may be substantially sanitized) outside of the PSS chamber, where it may be retrieved for further processing.

The PSS 1100 may be adapted for integration into an APAS cell 100, or configured for stand-alone (e.g., table-top) operation for use in a hospital pharmacy or similar environment. In the hospital pharmacy type of environment, pharmacy staff may prepare prescriptions by loading one or more objects to be sanitized on the platen 1105, perform the sanitizing, and retrieve the sanitized object for further processing after the platen 1105 rotates the object out of the chamber. Information indicating the form of medical container (e.g., size, shape, type) may be requested and/or obtained from a pharmacy computer system, for example, via a direct or networked data channel, which may be wired and/or wireless. As is known in the art, various data transfers may involve packets of data, and/or error detection and correction to ensure data integrity.

In some embodiments, the wall 1110 may further include multiple compartments (e.g., three, four, five, six, seven, eight or more) on the platen 1105. The walls may be uniformly distributed such that when any of the compartments is exposed to the UV radiation 1120, a portion of the wall 1110 is positioned to form a light seal.

In other embodiments, the platen 1105 may be a circular or non-circular track. It may advance substantially continuously, or in segments according to chambers. In some embodiments, the platen 1105 may advance in response to a user command, such as from a keypad or "start" button. In other embodiments, the platen 1105 may advance upon detecting the weight of one or more objects to be processed.

Similar to the discussion with reference to FIGS. 3A-3C, the PSS 1100 may be configured to include other arrangements of a baffle 1125, examples of which can be shown in FIGS. 11C, 11D, 11E, and 11F.

Other modifications may be made to the PSS 1000. For example, an illustrative embodiment of the PSS 1100 that includes a larger (or distributed) lamp system 1150 in combination with an illustrative embodiment of the baffle 1125 is shown in FIG. 12F. In this example, the UV radiation 1120 can be distributed over a broader area. The baffling 1125 and reflective surface on the platen 1105 can provide a broadly distributed UV radiation pattern over top and side surfaces of an object 1115b. Moreover, the platen 1105 is carrying two objects 1115a and 1115b. The object 1115b can be in the PSS chamber, and the object 1115a can be external to the PSS chamber. This multi-object carrying capability of the PSS system 1100 can promote efficient handling, for example, in a hospital pharmacy environment in which UV sanitizing processing time may affect productivity and throughput.

In another embodiment, the platen 1105 may be adapted to receive a tray of objects that are to be sanitized. For example, a tray of two or more vials to be sanitized may be placed on portion of the platen 1105 that is external to the PSS chamber. The trays may include carrying handles for convenient placement and/or stacking of vials. Such trays may be prepared in advance, and can later be efficiently batch processed, thereby saving time and labor for processing pharmaceutical admixtures.

To aid in aseptic processing, the entire PSS 1100 may be designed for use within an ISO class 5 clean air environment. Such an environment may be present, for example, within a containment cabinet in an APAS cell, or present in a hospital pharmacy laminar airflow hood. An air cooling system may be used, if needed, to dissipate the heat in the lamp housing 1170 or chamber 1175.

In addition to the above-described examples, UV sanitizing systems may be implemented using systems, methods, or computer program products other than the examples described above.

In various embodiments, a PSS system may communicate using suitable communication methods, equipment, and techniques. For example, the PSS control module may communicate with the APAS control unit and/or a hospital pharmacy network using point-to-point communication in which a message is transported directly from the source to the receiver over a dedicated physical link (e.g., fiber optic link, point-to-point wiring, daisy-chain). Other embodiments may transport messages by broadcasting to all or substantially all devices that are coupled together by a communication network, for example.

In some embodiments, each PSS system may be programmed with the same information and be initialized with substantially identical information stored in non-volatile memory. In other embodiments, one or more PSS systems may be custom configured to perform specific functions. For example, one PSS system may be configured to perform both custom and batch processing functions by responding to information about the objects to be sanitized.

In one aspect, an automated sanitizing system for a pharmacy environment for killing or incapacitating biocontaminants may present one or more objects to be sanitized. The system can include a chamber with a pulsed or constant wave form ultraviolet source. The system further can include an automated transport mechanism to place an object to be sanitized into the chamber for exposure to ultraviolet radiation from the ultraviolet source.

In various embodiments, the automated transport mechanism may further be to remove the object from the chamber after exposure to the ultraviolet radiation. The automated transport mechanism may include a robotic manipulator and/or a rotating platen. The automated transport mechanism may manipulate or move the object in response to a sequence of commands automatically generated by a processor executing a program of instructions.

Walls may substantially enclose the chamber, at least one wall having an opening for receiving the object and a portion of the transport mechanism. In some embodiments, the automated transport mechanism may provide at least a partial light seal around at least a portion of the opening.

The ultraviolet source may provide ultraviolet radiation in response to a trigger signal. The controller may generate one or more pulses or timed constant wave of a controlled waveform. The waveform may be controlled to provide a desired amplitude, shape, and/or intensity. The controller may generate a plurality of controlled pulses or constant wave according to a selected sanitizing routine. The selected sanitizing routine may correspond to characteristics, such as type, size, or manufacturer, of the object to be sanitized. The controller may receive messages over a communication link, and the messages may contain information about the characteristics of the object to be sanitized.

The object to be sanitized may include a portion of a vial, an IV bag, or a syringe. The biocontaminants to be killed or incapacitated may include one or more viruses, bacteria, and/or fungi. The ultraviolet radiation may include UV-A, UV-B, and/or UV-C wavelengths. Some embodiments may expose a fluid transfer port to be sanitized to a combined dose of both continuous and pulsed radiation over a predetermined period of time.

Some systems may be stand-alone or table top systems; other systems may be adapted for integration into an APAS.

In another aspect, a method of sanitizing at least one object surface may include generating a motion trajectory command to cause a transport mechanism to place an object within a chamber. The method may also include exposing at least a portion of the object to a dose of ultraviolet radiation.

In some embodiments, the dose of ultraviolet radiation may include one or more pulses or timed constant wave. The method may further include identifying a number of pulses or constant wave of ultraviolet radiation that is sufficient to kill or incapacitate one or more types of biocontaminants to a selected degree. The selected degree may be substantially all biocontaminants, such as at least 99.9999%, 99.99%, 99%, 95%, 90%, 80%, 75%, 70%, 60%, or at least about 50%. In some embodiments, between 1 and 100% of a particular biocontaminant may be killed or substantially incapacitated by the dose of ultraviolet radiation.

Figure 12:
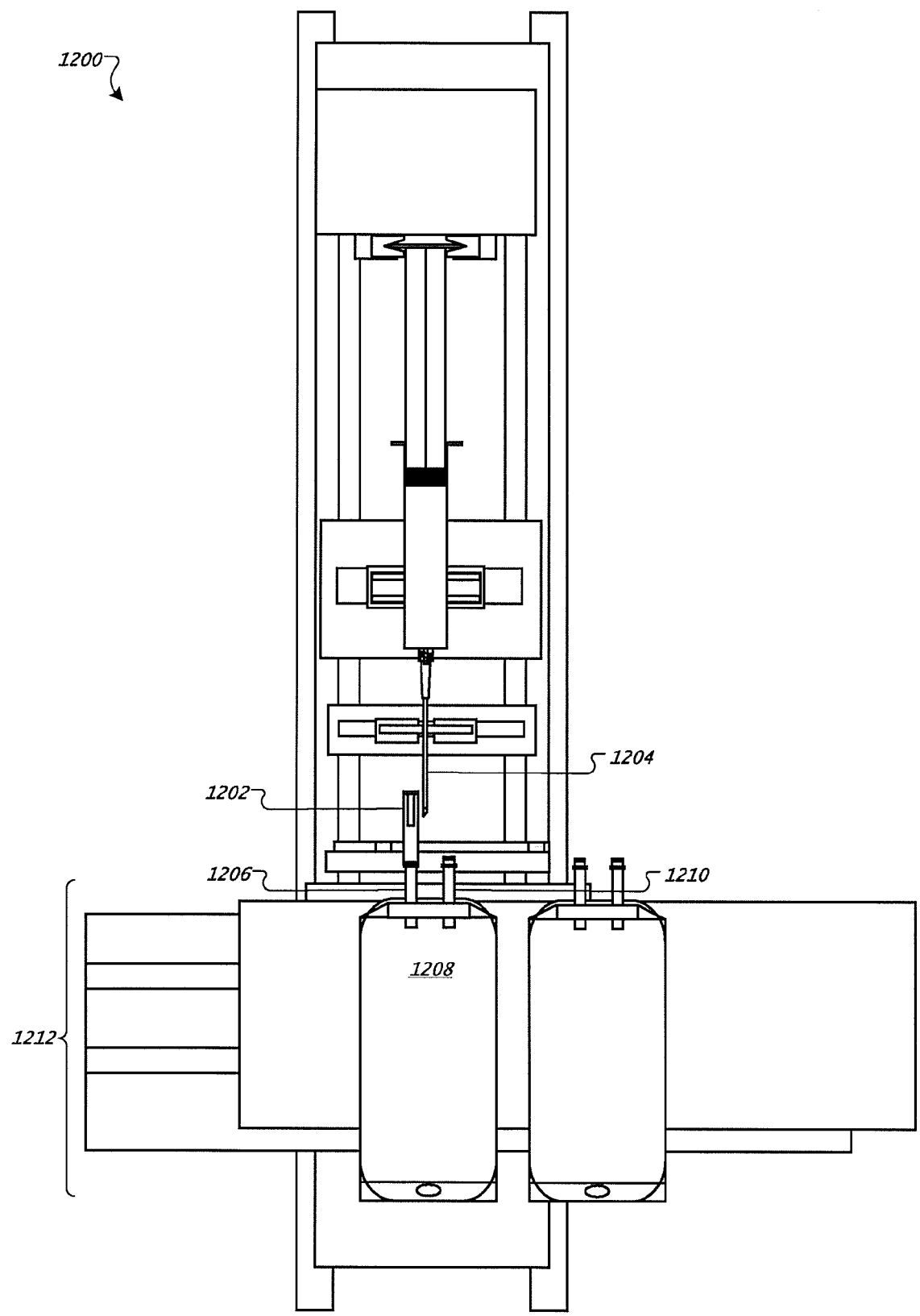
FIG. 12 shows an exemplary apparatus for performing a fluid transfer operation.

After the PSS sanitizes selected surfaces (e.g., drug vial ports, IV bag ports and syringes) using an ultraviolet (UV) light, a fluid transfer operation may be performed. FIG. 12 shows an example of an apparatus 1200 for performing a fluid transfer operation. Exemplary aspects of a similar syringe manipulator apparatus are described, for example, with reference to FIG. 7 in U.S. patent application Ser. No. 11/937, 846, entitled "Control of Fluid Transfer Operations," and filed by Doherty, et al. on Nov. 9, 2007, the entire contents of which are herein incorporated by reference. In some implementations, care should be taken during the fluid transfer operation to prevent a protective cover 1202 in the uncontrolled position from contaminating a selected surface (e.g., a needle 1204), or obstructing the insertion of the needle 1204 into a desired fluid port. The protective cover 1202 covers a first fluid transfer port 1206 of a container 1208. The container 1208 also includes a second fluid transfer port 1210. In one example, the fluid transfer operation is performed using the second fluid transfer port 1210 of the container 1208.

The container 1208 is held by a container manipulator 1212. The container manipulator 1212 can move in a horizontal and vertical direction to align a particular container and fluid transfer port with the needle 1204.

In an illustrative example, a draw from a vial may be performed as follows. First, the syringe plunger may be positioned to draw in a predetermined amount of air into the syringe barrel. This amount may be determined based on the required fluid volume of the prescription (first pull). The predetermined amount of air can replace the volume of fluid that is drawn with an approximately equal volume of air. So if 10 ml of fluid is being drawn, 10 ml of air can be pushed in to replace it. During this process, the system may estimate or monitor the 'headspace' in the vial. In a preferred embodiment, the method may maintain a slight negative pressure in the vial.

Second, the syringe plunger can be actuated to draw a predetermined amount of fluid from the vial. In this case it can generate a negative pressure. This can be limited so that pull does not exceed a force limit (e.g., by limiting motor current to a threshold level.) Third, the syringe plunger can be actuated to push a volume of air into the vial to replace the volume of fluid removed. Fourth, the syringe plunger can be retracted again to an amount approximately equal to the amount of air pumped into the vial. Fifth, the cycle can continue until the required amount of fluid is drawn into the syringe from the vial. Sixth, at the end of the cycling, the volume in the syringe can substantially match the required draw amount, and there can be a slight negative pressure in the vial.

In an illustrative example, a draw from an IV bag may be performed as follows. The IV bag may hang by its fill port on the indexer of a needle down syringe manipulator station. The indexer then moves the IV bag to a position under a syringe needle. The IV bag port then engages the syringe needle. A syringe plunger may be withdrawn so that air is drawn out of the IV bag and into the syringe. The syringe plunger may be withdrawn until the change in torque, for example, is detected and, in some embodiments, for some additional time to give margin on the draw resulting in a small amount of fluid draw and/or an IV bag that is negatively pressurized relative to ambient pressure. The indexer then lowers the IV bag.

Similar to the draw from a vial or IV bag as described above, one skilled in the art would readily appreciate that a dispense into a vial or IV bag may also be performed.

A number of implementations have been described. Nevertheless, it will be understood that various modifications may be made without departing from the spirit and scope. For example, advantageous results may be achieved if the steps of the disclosed techniques were performed in a different sequence, if components in the disclosed systems were combined in a different manner, or if the components were replaced or supplemented by other components. The functions and processes (including algorithms) may be performed in hardware, software, or a combination thereof, and some implementations may be performed on modules or hardware not identical to those described. Accordingly, other implementations are within the scope of the following disclosure.

What is claimed is:

1. A system to automate pharmaceutical compounding, the system comprising:
   a chamber;
   an automated system to transport medical containers within the chamber;
   a compounding system disposed in the chamber to transfer medicaments between medical containers; and
   a sanitization system to substantially reduce bioactivity on at least a portion of a first fluid transfer port of a first form of medical container and a second fluid transfer port of a second form of medical container, the sanitization system comprising:
     at least one radiation source to supply a dose of radiation;
     a first radiation seal assembly having a first aperture and being configured to engage the first fluid transfer port of the first form of medical container;
     at least a second radiation seal assembly substantially different from the first radiation seal assembly, wherein the second radiation seal assembly has a second aperture and is configured to engage the second fluid transfer port of the second form of medical container, the second form medical container being substantially different from the first form of medical container;
     a controller to determine which radiation seal assembly corresponds to a third fluid transfer port to be sanitized, wherein the third fluid transfer port is part of a third medical container, the third medical container being one of the first form and the second form; and
     an actuator to bring the portion of the third fluid transfer port to be sanitized into optical communication with the radiation source through the aperture of the determined radiation seal assembly.

2. The system of claim 1 further comprising a control system to regulate a pressure in the chamber.

3. The system of claim 1, wherein the radiation source comprises an ultraviolet (UV) source.

4. The system of claim 3, wherein the UV source is configured to supply a dose of UV radiation to reduce at least 99% of biocontaminants.

5. The system of claim 1, wherein the sanitization system further comprises at least one optical conduit configured to transmit radiation from the radiation source to the portion of the third fluid transfer port to be sanitized.

6. The system of claim 1, wherein each radiation seal assembly is configured to not touch the portion of the third fluid transfer port to be sanitized.

7. The system of claim 1, wherein at least one radiation seal assembly comprises a gasket formed around the aperture.

8. The system of claim 7, wherein the first radiation seal assembly or the second radiation seal assembly further comprises chamfered guides to promote engagement between the third fluid port and the gasket.

9. The system of claim 7, wherein the gasket comprises a flexible UV blocking material.

10. The system of claim 7, wherein the sanitization system further comprises a pressure chamber configured to substantially form a light seal between the third fluid transfer port and the gasket.

11. The system of claim 1, wherein the sanitization system further comprises an interlock to determine whether the radiation source can be activated to supply the dose of radiation.

12. The system of claim 1 further comprising a fluid transfer system that can transfer fluid through the sanitized portion of the third fluid transfer port.

13. The system of claim 1, wherein at least one of the first form of medical container and the second form of medical container comprises a drug vial, an IV bag, or a syringe.

14. The system of claim 1, wherein an interior of the chamber is substantially aseptic.

15. The system of claim 14, wherein the interior of the chamber meets ISO Class 5 clean room standards.

16. The system of claim 1, wherein the third medical container is disposed on a moveable platen.

17. The system of claim 1, wherein the first radiation seal assembly and the second radiation seal assembly are coupled to a rotating carousel.

18. The system of claim 17, wherein the rotating carousel is configured to receive removable or interchangeable radiation seal assemblies.

19. The system of claim 1, wherein the sanitization system further comprises at least one optical sensor to detect the presence of the radiation.

20. The system of claim 1, further comprising a pharmacy computer system, wherein the controller can obtain information indicating the form of the third medical container from the pharmacy computer system.

21. The system of claim 1, wherein the sanitization system further comprises a cooling and venting system including at least one HEPA fan filter unit.

22. A sanitization system to substantially reduce bioactivity on at least a portion of a first fluid transfer port of a first form of medical container and a second fluid transfer port of a second form of medical container, the system comprising:
at least one radiation source to supply a dose of radiation;
a first radiation seal assembly having a first aperture and being configured to engage the first fluid transfer port of the first form of medical container;
at least a second radiation seal assembly substantially different from the first radiation seal assembly, wherein the second radiation seal assembly has a second aperture and is configured to engage the second fluid transfer port of the second form of medical container, wherein the second form of medical container has particular shape substantially different from the first form of medical container; a controller to determine which radiation seal assembly corresponds to a third fluid transfer port to be sanitized, wherein the third fluid transfer port is part of a third medical container, the third medical container being one of the first form and the second form; and
an actuator to bring the portion of the third fluid transfer port to be sanitized into optical communication with the radiation source through the aperture of the radiation seal assembly determined to correspond to the third fluid transfer port.

23. The sanitization system of claim 22, wherein the radiation source comprises an ultraviolet (UV) source.

24. The system of claim 23, wherein the UV source is configured to supply a dose of UV radiation to reduce at least 99% of biocontaminants.

25. The sanitization system of claim 22, wherein the sanitization system further comprises at least one optical conduit configured to transmit radiation from the radiation source to the portion of the third fluid transfer port to be sanitized.

26. The sanitization system of claim 22, wherein each radiation seal assembly is configured to not touch the portion of the third fluid transfer port to be sanitized.

27. The sanitization system of claim 22, wherein at least one of the first radiation seal assembly and the second radiation seal assembly comprises a gasket formed around the aperture.

28. The sanitization system of claim 27, wherein the at least one of the first radiation seal assembly and the second radiation seal assembly further comprises chamfered guides to promote engagement between the third fluid port to be sanitized and the gasket.

29. The sanitization system of claim 27, wherein the gasket comprises a flexible UV blocking material.

30. The sanitization system of claim 27 further comprising a pressure chamber configured to substantially form a light seal between the third fluid transfer port to be sanitized and the gasket.

31. The sanitization system of claim 22 further comprising an interlock to determine whether the radiation source can be activated to supply the dose of radiation.

32. The sanitization system of claim 22, wherein at least one of the first form of medical container and the second form of medical container comprises a drug vial, an IV bag, or a syringe.

33. The sanitization system of claim 22 further comprising a pressure controlled chamber that substantially contains the radiation source, the first radiation seal assembly, the second radiation seal assembly, and the actuator.

34. The sanitization system of claim 33, wherein an interior of the pressure controlled chamber is substantially aseptic.

35. The sanitization system of claim 33, wherein the interior of the pressure controlled chamber meets ISO Class 5 clean room standards.

36. The sanitization system of claim 33, further comprising a cooling and venting system configured to manage an environment of the pressure controlled chamber, wherein the cooling and venting system includes at least one HEPA fan filter unit.

37. The sanitization system of claim 22, wherein the controller is coupled to receive indentifying information about the third medical container from a pharmaceutical prescription database.

38. The system of claim 22, further comprising a pharmacy computer system, wherein the controller can obtain information indicating the form of the third medical container from the pharmacy computer system.

39. The system of claim 22, wherein the controller generates a sanitizing profile tailored to sanitize the third medical container based on one or more of a size, type, and shape of the third medical container.

40. The sanitization system of claim 22, wherein the third medical container is disposed on a moveable platen.

41. The sanitization system of claim 22, wherein the first radiation seal assembly and the second radiation seal assembly are coupled to a rotating carousel.

42. The sanitization system of claim 22, further comprising at least one optical sensor to detect the presence of the radiation.

43. A method of substantially sanitizing at least a portion of a first fluid transfer port of a first form of medical container and at least a portion of a second fluid transfer port of a second form of medical container, the method comprising the steps of:

provided a sanitization system having at least one radiation source, a first radiation seal assembly having a first aperture and being configured to engage the first fluid transfer port of the first form of medical container, and a second radiation seal assembly substantially different from the first radiation seal assembly, wherein the second radiation seal assembly has a second aperture and is configured to engage the second fluid transfer port of the second form of medical container, wherein the second form of medical container has a particular shape substantially different from the first form of medical container;

retrieving a third medical container to be sanitized, wherein the third medical container has one of the first form and the second form;

determining, using a controller, which radiation seal assembly corresponds to the third medical container;

engaging the third medical container with the determined radiation seal assembly; and supplying a predetermined dose of radiation from the radiation source to a portion of a third fluid transfer port of the third medical container to be sanitized to substantially reduce bioactivity thereon.

44. The method of claim 43, wherein the radiation source comprises an ultraviolet (UV) source.

45. The method of claim 44, wherein the UV source is configured to supply a dose of UV radiation to reduce at least 99% of biocontaminants.

46. The method of claim 45, further comprising, upon determining the corresponding radiation seal assembly, rotating the rotating carousel to align the corresponding radiation seal assembly for engagement with the third medical container.

47. The method of claim 43, wherein retrieving the third medical container comprises actuating an automated transfer mechanism to bring the third fluid transfer port to be sanitized into substantial register with the determined radiation seal assembly.

48. The method of claim 43, wherein supplying the predetermined dose comprises transmitting the dose through an optical conduit.

49. The method of claim 43, wherein engaging the third medical container with the determined radiation seal assembly comprises substantially forming a light seal between the third medical container to be sanitized and the determined radiation seal assembly using a pressure chamber.

50. The method of claim 43, wherein the third medical container comprises a drug vial, an IV bag, or a syringe.

51. The method of claim 43 further comprising transferring fluid through the sanitized portion of the third fluid transfer port.

52. The method of claim 43, wherein each radiation seal assembly is configured to not touch the portion of the third fluid transfer port to be sanitized.

53. The method of claim 43, further comprising disposing the third medical container on a movable platen, wherein engaging the third medical container comprises moving the movable platen to put the third medical container in an engaged position in relation to the determined radiation seal assembly.

54. The method of claim 43, wherein the first radiation seal assembly and the second radiation seal assembly are coupled to a rotating carousel.

55. The method of claim 43, wherein the sanitization system further comprises at least one optical sensor to detect the presence of the radiation.

56. The method of claim 43, further comprising obtaining information indicating the form of the third medical container from a pharmacy computer system.

* * * * *